(12) United States Patent
Chau et al.

(10) Patent No.: US 12,109,307 B2
(45) Date of Patent: Oct. 8, 2024

(54) COMPOSITIONS AND METHODS FOR CONTROLLED RELEASE OF TARGET AGENT

(71) Applicant: The Hong Kong University Of Science and Technology, Kowloon (HK)

(72) Inventors: Ying Chau, Kowloon (HK); Chi Ming Laurence Lau, Kowloon (HK); Yu Yu, Kowloon (HK)

(73) Assignee: THE HONG KONG UNIVERSITY OF SCIENCE AND TECHNOLOGY, Kowloon (HK)

( * ) Notice: Subject to any disclaimer, the term of this patent is extended or adjusted under 35 U.S.C. 154(b) by 706 days.

(21) Appl. No.: 17/261,411

(22) PCT Filed: Jul. 19, 2019

(86) PCT No.: PCT/CN2019/096795
§ 371 (c)(1),
(2) Date: Jan. 19, 2021

(87) PCT Pub. No.: WO2020/015737
PCT Pub. Date: Jan. 23, 2020

(65) Prior Publication Data
US 2021/0220266 A1    Jul. 22, 2021

Related U.S. Application Data

(60) Provisional application No. 62/701,122, filed on Jul. 20, 2018.

(51) Int. Cl.
| | |
|---|---|
| *A61K 47/20* | (2006.01) |
| *A61K 9/00* | (2006.01) |
| *A61K 9/06* | (2006.01) |
| *A61K 47/36* | (2006.01) |
| *C08L 5/02* | (2006.01) |

(52) U.S. Cl.
CPC ............. *A61K 9/06* (2013.01); *A61K 9/0019* (2013.01); *A61K 47/20* (2013.01); *A61K 47/36* (2013.01); *C08L 5/02* (2013.01)

(58) Field of Classification Search
CPC ........ A61K 9/06; A61K 9/0019; A61K 47/20; A61K 47/36; A61K 2039/545; C08L 5/02; C08L 81/02; C07K 16/22
See application file for complete search history.

(56) References Cited

U.S. PATENT DOCUMENTS

| 7,829,118 B1 | 11/2010 | Gravett et al. |
| 9,205,150 B2 | 12/2015 | Jarrett et al. |
| 2011/0033540 A1 | 2/2011 | Daniloff et al. |
| 2012/0114615 A1 | 5/2012 | Burdick et al. |
| 2013/0071462 A1 | 3/2013 | Jarrett et al. |

FOREIGN PATENT DOCUMENTS

| CN | 105688284 A | 6/2016 | |
| JP | 2012-506840 A | 3/2012 | |
| WO | WO 00/78285 A1 * | 12/2000 | ............... A61K 9/00 |

OTHER PUBLICATIONS

Hiemstra et al (Novel in Situ Forming, Degradable Dextran Hydrogels by Michael Addition Chemistry: Synthesis, Rheology, and Degradation, Macromolecules 2007, 40, 1165-1173, published on Jan. 11, 2007).*
International Search Report, Application No. PCT/CN2019/096795, mailed Oct. 24, 2019.
Jahanmir, G., et al., Stochastic Modeling of Degradation Behavior of Hydrogels, Macromolecules, ACS Publications, American Chemical Society, 51, 3941-3952, May 15, 2018.
Yu, Y., et al., Injectable Chemically Crosslinked Hydrogel for the Controlled Release of Bevacizumab in Vitreous: A 6-Month In Vivo Study, Translational Vision Science & Technology, vol. 4, No. 2, Article 5, pp. 1-11, Mar. 10, 2015.
Yu, Y., et al., Formulation of In Situ Chemically Cross-Linked Hydrogel Depots for Protein Release: From the Blob Model Perspective, BioMacromolecules, ACS Publications, American Chemical Society, 16, pp. 56-65, Oct. 14, 2014 (2015).

* cited by examiner

*Primary Examiner* — Gregory Listvoyb
(74) *Attorney, Agent, or Firm* — Honigman LLP; Thomas A. Wootton, Esq.; Jonathan P. O'Brien

(57) ABSTRACT

The present disclosure provides compositions and methods for controlled release of macromolecules (such as proteins and polypeptides). The present disclosure also provides method for preparing and using the same.

6 Claims, 15 Drawing Sheets

1: ester linker: DTT-VMA-DTT
2: ester linker: DTE-VMA-DTE
3: ester linker: DTP-VMA-DTP

COMPOSITIONS AND METHODS FOR CONTROLLED RELEASE OF TARGET AGENT

CROSS-REFERENCE TO RELATED APPLICATIONS

This application is a National Stage Application and claims priority under 35 U.S.C. § 371 to Patent Cooperation Treaty application PCT/CN2019/096795, filed Jul. 19, 2019, which claims the benefit of provisional US application U.S. 62/701,122, filed Jul. 20, 2018. Priority is claimed to these applications and the disclosures of these prior applications are considered part of the disclosure of this application and to the extent allowed the entire contents of the aforementioned applications are incorporated herein.

BACKGROUND OF THE INVENTION

Macromolecule (e.g., proteins, polypeptides or aptamers) based therapeutics are inherently labile, susceptible to degradation, denaturation and aggregation, which all lead to loss of functionality. Repeated dosing is the current strategy to tackle such limitations. Sustained release over a relatively longer period of time (e.g., 6~12 months) is one of the alternatives superior to the multi-dosing strategy.

To achieve sustained release, one approach is to modify the macromolecule itself (e.g., proteins, polypeptides or aptamers) to extend its circulation time and/or to increase its stability. However, such an approach is molecule specific, and often requires huge financial and time investment.

People have also attempted to use hydrogels for delivery of macromolecules (e.g., proteins, polypeptides or aptamers). However, currently available hydrogel systems cannot serve the unmet needs very well. Chemically crosslinked hydrogels usually release loaded macromolecules in a few days. In physically entangled systems, the longest in vitro release duration was no longer than about 2 months.

Accordingly, a versatile, effective, and/or customizable approach is highly needed to achieve sustained release of macromolecules, such as proteins, polypeptides and aptamers.

SUMMARY OF THE INVENTION

The present disclosure provides compositions and methods for controlled release of macromolecules (such as proteins and polypeptides). With the systems and methods of the present disclosure, macromolecule releasing rate may be predicted and controlled. The macromolecules may be retained within a structure (e.g., hydrogel) formed by polymers, which may be degraded (e.g., through hydrolytic cleavage) during an extended period of time (e.g., over days, weeks, or even months). The degradation may occur under physiological conditions. The polymers as well as its degradation products may be biocompatible. The polymer structure (e.g., hydrogel) may be formed in situ, for example, a composition (e.g., a liquid formulation) capable of forming the polymer structure (e.g., hydrogel) may be introduced (injected) into a tissue, and then, the polymer structure (e.g., hydrogel) may be formed in situ within the tissue upon being introduced.

In one aspect, the present disclosure provides a composition comprising one or more hydrogel forming polymers, the hydrogel enables sustained release of a target agent, at least one of the one or more hydrogel forming polymers comprises a degradable backbone, and wherein the degradable backbone comprises precursor polymers linked by a degradable linker.

In some embodiments, the degradable linker is hydrolysable, enzymatically degradable, or otherwise cleavable.

In some embodiments, the hydrogel forming polymer is hydrophilic and/or water soluble.

In some embodiments, the degradable linker comprises a hydrolysable functional group.

In some embodiments, the hydrolysable functional group is selected from an ester group, an anhydride group, and an amide group.

In some embodiments, the ester group is selected from an oxyester group and a thiolester group.

In some embodiments, the hydrogel forming polymer is selected from the group consisting of a polysaccharide, a polyethylene glycol, a derivative thereof, and any combinations thereof.

In some embodiments, the hydrogel forming polymer is selected from the group consisting of a hyaluronic acid, a chitosan, a chondroitin sulfate, an alginate, a carboxymethylcellulose, a dextran, a polyethylene glycol, a derivative thereof, and any combinations thereof.

In some embodiments, the hydrogel forming polymer is selected from the group consisting of a dextran, a hyaluronic acid, a polyethylene glycol, a derivative thereof, and any combinations thereof.

In some embodiments, the hydrogel forming polymer comprises a derivative modified with one or more modifications selected from the group consisting of an acrylate, a methacrylate, a maleimide, a vinylsulfone, a thiol, an amine, and any combinations thereof.

In some embodiments, the hydrogel forming polymer derivative has an average degree of modification (DM) of less than about 20%.

In some embodiments, the composition comprises at least a first hydrogel forming polymer derivative and a second hydrogel forming polymer derivative, wherein the first hydrogel forming polymer derivative comprises a first modification and the second hydrogel forming polymer derivative comprises a second modification, the first modification is different from the second modification, and the first polymer derivative is capable of reacting with the second polymer derivative to form the hydrogel.

In some embodiments, a mass ratio between the first hydrogel forming polymer derivative and the second hydrogel forming polymer derivative in the composition is from about 3:1 to about 1:3.

In some embodiments, a molar ratio between the first hydrogel forming polymer derivative and the second hydrogel forming polymer derivative in the composition is from about 10:1 to about 1:10.

In some embodiments, a volume ratio between the first hydrogel forming polymer derivative and the second hydrogel forming polymer derivative in the composition is from about 3:1 to about 1:3.

In some embodiments, the first hydrogel forming polymer derivative has a first DM, the second hydrogel forming polymer derivative has a second DM, and a ratio between the first DM and the second DM is from about 3:1 to about 1:3.

In some embodiments, the first modification and the second modification are each independently selected from the group consisting of an acrylate, a methacrylate, a maleimide, a vinylsulfone, a thiol, an amine, and any combinations thereof.

In some embodiments, the first hydrogel forming polymer derivative is a dextran derivative modified with one or more vinylsulfone groups, a hyaluronic acid derivative modified with one or more vinylsulfone groups, a polyethylene glycol derivative modified with one or more vinylsulfone groups, or a combination thereof, the second hydrogel forming polymer derivative is a dextran derivative modified with one or more thiol groups, a hyaluronic acid derivative modified with one or more thiol groups, a polyethylene glycol derivative modified with one or more thiol groups, or a combination thereof.

In some embodiments, the first hydrogel forming polymer derivative and/or the second hydrogel forming polymer derivative comprises the degradable backbone.

In some embodiments, the hydrogel forming polymer has a weight averaged molecular weight from about 10 kDa to about 500 kDa.

In some embodiments, the composition is a powder.

In some embodiments, the composition is a liquid composition, and a concentration of the one or more hydrogel forming polymers in the liquid composition is from about 10% w/v to about 40% w/v.

In some embodiments, the hydrogel forming polymer comprising the degradable backbone has a polydispersity of 4 or less.

In some embodiments, the hydrogel forming polymer comprising the degradable backbone is formed by crosslinking the precursor polymers with the degradable linker, wherein the degradable linker enables formation of degradable linkage between the precursor polymers.

In some embodiments, the precursor polymer is hydrophilic and/or water soluble.

In some embodiments, the precursor polymer is non-hydrolysable, enzymatically non-degradable, or otherwise non-cleavable.

In some embodiments, the precursor polymer is selected from the group consisting of a polysaccharide, a polyethylene glycol, a derivative thereof, and any combinations thereof.

In some embodiments, the precursor polymer is selected from the group consisting of a dextran, a hyaluronic acid, a polyethylene glycol, a derivative thereof, and any combinations thereof.

In some embodiments, the precursor polymer is a derivative comprising one or more modifications, and a degree of modification of the precursor polymer is less than about 20%.

In some embodiments, the composition wherein for forming the hydrogel forming polymer comprising the degradable backbone, a molar ratio between the degradable linker and the modification on the precursor polymer is from about 1:1 to about 1:10.

In some embodiments, the composition wherein for forming the hydrogel forming polymer comprising the degradable backbone, an amount of the degradable linker is equivalent to crosslinking about 1-5 the modification per the precursor polymer.

In some embodiments, the modification of the precursor polymer is selected from the group consisting of an acrylate, a methacrylate, a maleimide, a vinylsulfone, a thiol, an amine, and any combinations thereof.

In some embodiments, the degradable linker comprises two or more modifications, and a degree of modification of the degradable linker is less than about 30%.

In some embodiments, the modification of the degradable linker is selected from the group consisting of an acrylate, a methacrylate, a maleimide, a vinylsulfone, a thiol, an amine, and any combinations thereof.

In some embodiments, the precursor polymer is a dextran derivative modified with one or more vinylsulfone groups, a hyaluronic acid derivative modified with one or more vinylsulfone groups, a polyethylene glycol derivative modified with one or more vinylsulfone groups, or a combination thereof, and the degradable linker comprises two or more thiol group modifications.

In some embodiments, the precursor polymer is a dextran derivative modified with one or more thiol groups, a hyaluronic acid derivative modified with one or more thiol groups, a polyethylene glycol derivative modified with one or more thiol groups, or a combination thereof, and the degradable linker comprises two or more vinylsulfone group modifications.

In some embodiments, the degradable linker is selected from a divinyl methacrylate, a divinyl acrylate, and a derivative thereof.

In some embodiments, the degradable linker is selected form the following groups:

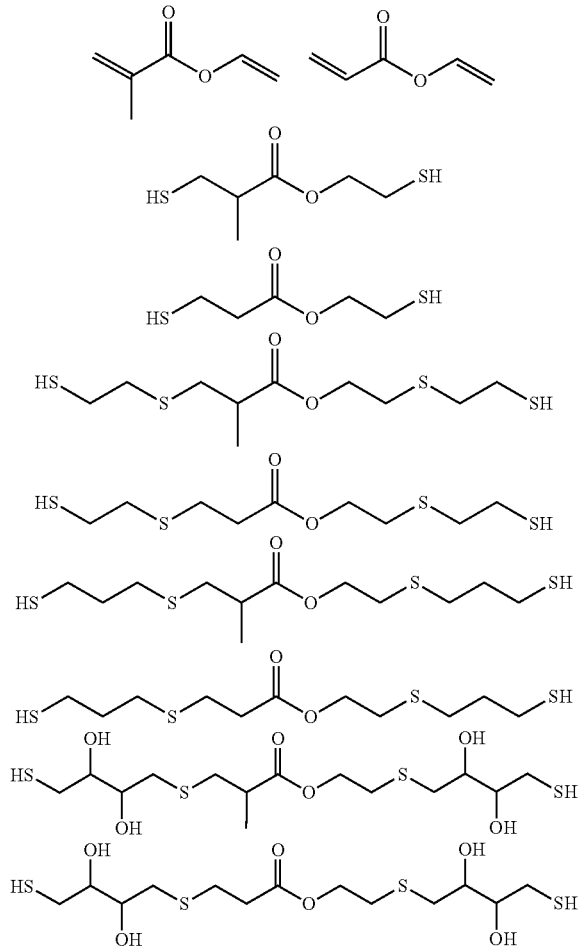

In some embodiments, the precursor polymer has a weight averaged molecular weight of 2 kDa to 20 kDa.

In another aspect, the present disclosure provides a hydrogel for sustained release of a target agent, wherein the hydrogel is formed with the composition.

In some embodiments, the hydrogel further comprises the target agent.

In some embodiments, the target agent comprises a macromolecule.

In some embodiments, the target agent comprises a protein or a polypeptide.

In some embodiments, about less than 30% of the target agent is cumulatively released within an initial 24 hours from the hydrogel, and the remaining portion of the target agent is cumulatively released from the hydrogel in about 3 to about 36 months.

In another aspect, the present disclosure provides a method for producing a hydrogel, comprising: a) providing the composition; b) mixing the composition with a buffer to form a polymer solution; and c) subjecting the polymer solution to a condition enabling formation of the hydrogel.

In some embodiments, the subjecting comprises injecting the polymer solution in a subject in need thereof.

In some embodiments, the subjecting comprises incubating the composition at about 30° C. to about 45° C.

In some embodiments, the polymer solution further comprises the target agent.

In another aspect, the present disclosure provides a method for producing the composition comprising: a) cross-linking the precursor polymer with the degradable linker to obtain the hydrogel forming polymer comprising the degradable backbone; and b) mixing the hydrogel forming polymer comprising the degradable backbone with an additional polymer, wherein the additional polymer is capable of reacting with the hydrogel forming polymer comprising the degradable backbone under a condition enabling formation of the hydrogel.

In another aspect, the present disclosure provides a method for sustained release of a target agent, comprising mixing the target agent with a composition to obtain a mixture, and subjecting the mixture to a condition enabling formation of a hydrogel capable of sustained release of the target agent.

In another aspect, the present disclosure provides a method for sustained release of a target agent, comprising enclosing the target agent in the hydrogel.

In another aspect, the present disclosure provides a kit, comprising: a) the composition; and b) a target agent to be sustained released by a hydrogel formed with the composition of a).

In another aspect, the present disclosure provides a use of the composition for making a hydrogel.

In another aspect, the present disclosure provides a use of the composition or the hydrogel for sustained release of a target agent.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are employed, and the accompanying drawings (also "figure" and "FIG." herein), of which:

FIG. 21A-22B illustrate the protein (Fitc-labled Immunoglobulin G) release profile from the junction-lysable and backbone-lysable hydrogel formulations, and the combined mixture of the two at different ratios.

DETAILED DESCRIPTION

Figure 1:
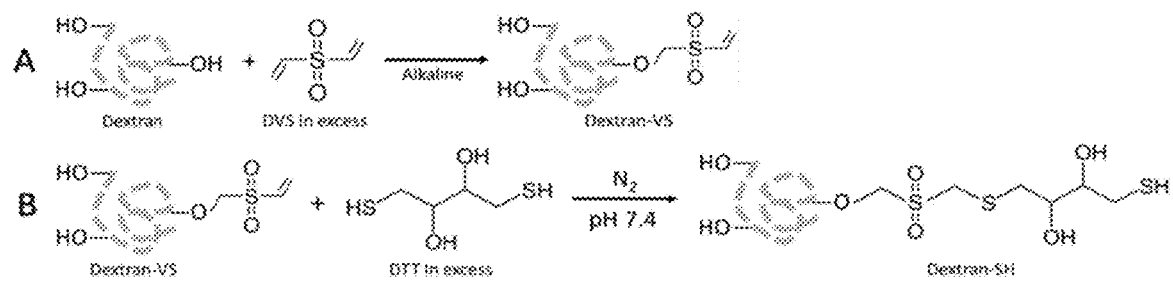
FIG. 1A-1B illustrate synthesis schemes of vinyl sulfone grafted dextran (DX-VS) (FIG. 1A); and thiol grafted dextran (DX-SH) (FIG. 1B).

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Definition

The term "polymer", as used herein, generally refers to a chemical compound or mixture of compounds formed by polymerization and consisting essentially of repeating structural units.

The term "hydrogel", as used herein, generally refers to a gel or gel-like structure comprising one or more polymers suspended in an aqueous solution (e.g., water). All hydrogels possess some level of physical attraction between macromers as a result of hydrogen bonding and entanglements amongst one another. Usually a hydrogel intended for tissue engineering applications may be strengthened through additional electrostatic interactions or chemical cross-linking.

The term "sustained release", as used herein, generally refers to a process for releasing a target agent relatively slowly over an extended period of time (e.g., in days, weeks, or months).

The term "a degradable backbone", as used herein, generally refers to a polymer structure (e.g., a polymer chain) that can be degraded under physiological conditions (e.g about 37° C. and pH is about 6.5~8). In some cases, the backbone is partially degradable, formed by non-degradable polymers (e.g., precursor polymers) linked together through degradable linkers. The degradation may be chemical degradation (e.g hydrolytic cleavage) or biological degradation (e.g. enzymatic cleavage). In the present disclosure, the degradable backbone may also be referred to as backbone-lysable.

The term "hydrolysable backbone", as used herein, generally refers to a polymer structure (e.g., a polymer chain) that can be at least partially hydrolyzed. For example, the hydrolysable backbone may be formed by crosslinking linear, or branched non-hydrolysable precursor polymers using hydrolysable groups and/or crosslinkers comprising esters. The linear, or branched precursor polymers may be modified with one or more modifications. For instance, the hydrolysable functional group may be selected from an ester group, an anhydride group, and an amide group. For instance, the hydrolysable backbone may be distinct from those polymers grown from polymerization of monomers, such as Polylactic Acid (PLA) or poly(lactic-co-glycolic acid) (PLGA).

The term "hydrogel forming polymer", as used herein, generally refers to a naturally occurring polymer or a synthetic polymer capable of forming a hydrogel. The hydrogel forming polymer can be classified according to their synthetic origins, composition, electrostatic nature and gel forming mechanism. In some cases, non-degradable hydrogel-forming polymers may have degradable regions built into their structure to impart finely controlled degradability.

The term "hydrolysable", as used herein, generally refers to a property of capable to be hydrolyzed. For example, a property of capable to be hydrolyzed at physiological temperature (30° ° C. to 40° C.) and pH (6.5 to 7.5) without catalyst, eg enzymes. Usually, hydrolysis is a chemical process in which a molecule of water is added to a substance. In such reactions, one fragment of the molecule gains a hydrogen ion, and chemical bonds in a compound may be broken down.

The term "hydrophilic", as used herein, generally refers to having an affinity for water, able to absorb or be wetted by water. A hydrophilic molecule or portion of a molecule is one whose interactions with water and other polar substances are more thermodynamically favorable than their interactions with oil or other hydrophobic solvents.

The term "ester group", as used herein, generally refers to a chemical group derived from an acid (organic or inorganic) in which at least one —OH (hydroxyl) group is replaced by an —O-alkyl (alkoxy) group. For example, the ester group may be selected from an oxyester group and a thiolester group.

The term "average degree of modification (DM)", as used herein, generally refers to the number of pendant groups per 100 repeating unit in a polymer. DM may reflect the degrees of modification of hydrogel forming polymer derivative.

The term "polydispersity", as used herein, generally refers to a characteristic of polymers in term of disperse, or non-uniform, if the chain length of the polymer varies over a wide range of molecular masses. The polydispersity index ($Đ_X$) may be calculated according to degree of polymerization. $Đ_X$=Mw/Mn, where Mw is the weight average degree of polymerization and Mn is number average molecular weight. For example, the hydrogel forming polymer comprising the degradable backbone has a polydispersity of 4 or less.

The term "crosslink", as used herein, generally refers to a bond that links one polymer chain to another. They can be covalent bonds or ionic bonds. "Polymer chains" may refer to synthetic polymers or natural polymers (such as proteins). In polymer chemistry, when a synthetic polymer is said to be "cross-linked", it usually means that the entire bulk of the polymer has been exposed to the cross-linking method. The resulting modification of mechanical properties depends strongly on the cross-link density. Crosslinks may be formed by chemical reactions that are initiated by heat, pressure, change in pH, or radiation.

The term "precursor polymer", as used herein, generally refers to a polymer used to form another polymer structure or to be further modified. This material is capable of further polymerization by reactive groups to form structures of higher molecular weight.

The term "composition", as used herein, generally refers to a product (liquid or solid-state) of various elements or ingredients.

The term "about", when used in the context of numerical values, generally refers to a value less than 1% to 15% (e.g., less than 1%, less than 2%, less than 3%, less than 4%, less than 5%, less than 6%, less than 7%, less than 8%, less than 9%, less than 10%, less than 11%, less than 12%, less than 13%, less than 14%, or less than 15%) above or below an indicated value.

Where a range of values (e.g., a numerical range) is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As used herein, the singular forms "a," "and," and "the" include plural referents unless the context clearly dictates otherwise. Thus, for example, reference to "a particle" includes a plurality of such particles and reference to "the sequence" includes reference to one or more said sequences and equivalents thereof known to those skilled in the art, and so forth.

As will be understood by those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. This is intended to provide support for all such combinations.

The present disclosure provides compositions comprising one or more hydrogel forming polymers and methods for making and using the same. And the present disclosure provides a hydrogel and methods for making and using the same.

In one aspect, the present disclosure provides a composition which may comprise one or more (e.g. one, two, three, four, five, six, seven, eight, nine, ten or more) hydrogel forming polymers, said hydrogel enables sustained release of a target agent, at least one of said one or more (e.g. one, two, three, four, five, six, seven, eight, nine, ten or more) hydrogel forming polymers comprises a degradable backbone, and wherein said degradable backbone comprises precursor polymers linked by a degradable linker.

In the present disclosure, the degradable linker may be hydrolysable, enzymatically degradable, or otherwise cleavable.

In the present disclosure, the hydrogel forming polymer may be hydrophilic and/or water soluble.

In the present disclosure, the degradable linker may comprise a hydrolysable functional group. For example, the hydrolysable functional group may be selected from an ester group, an anhydride group, and an amide group.

In the present disclosure, the ester group may be selected from an oxyester group and a thiolester group. For example, the oxyester group may have a functional group of —COOR, and the thiolester group may have a functional group of R—S—CO—R', which may be the product of esterification between a carboxylic acid and a thiol.

In some cases, the hydrogel forming polymer may be selected from the group consisting of a polysaccharide, a polyethylene glycol, a derivative thereof, and any combinations thereof.

In some cases, the polysaccharide may be homoglycans, i.e. polysaccharides having a main chain consisting of one single sugar, e.g. colominic acid; or, may be heteroglycans, i.e. polysaccharides having more than one sugar residue in the main chain in either alternating or less regular sequence; e.g. Gellans; Succinoglycans; Arabinogalactans; Tragacanth or gum tragacanth or traganth from *Astragalus*; Gum Karaya from *Sterculia urens*; Gum Ghatti from *Anogeissus latifolia* and the derivatives thereof.

In some cases, the structure of polyethylene glycol may be commonly expressed as H—(O—CH$_2$—CH$_2$)$_n$—OH. The polyethylene glycol may be in a wide range of molecular weights from 300 g/mol to 10,000,000 g/mol.

In the present disclosure, the hydrogel forming polymer may be selected from the group consisting of a hyaluronic acid, a chitosan, a chondroitin sulfate, an alginate, a carboxymethylcellulose, a dextran, a polyethylene glycol, a derivative thereof, and any combinations thereof.

In some cases, the hydrogel forming polymer may be selected from the group consisting of a dextran, a hyaluronic acid, a polyethylene glycol, a derivative thereof, and any combinations thereof.

In the present disclosure, the hydrogel forming polymer comprises a derivative modified with one or more modifications selected from the group consisting of an acrylate, a methacrylate, a maleimide, a vinylsulfone, a thiol, an amine, and any combinations thereof.

In the present disclosure, the hydrogel forming polymer derivative may have an average degree of modification (DM) of less than about 20% (e.g. less than about 20%, less than about 19%, less than about 18%, less than about 17%, less than about 16%, less than about 15%, less than about 14%, less than about 13%, less than about 12%, less than about 11%, less than about 10%, less than about 8%, less than about 6%, less than about 4%, less than about 2%, less than about 0.5% or less).

In the present disclosure, the composition may have at least a first hydrogel forming polymer derivative and a second hydrogel forming polymer derivative, wherein the first hydrogel forming polymer derivative comprises a first modification and the second hydrogel forming polymer derivative may comprise a second modification, the first modification may be different from the second modification, and the first polymer derivative may be capable of reacting with the second polymer derivative to form the hydrogel.

In the present disclosure, a mass ratio between the first hydrogel forming polymer derivative and the second hydrogel forming polymer derivative in the composition may be from about 3:1 to about 1:3 (e.g. from about 3:1 to about 1:3, from about 3:1.5 to about 1:3, from about 3:2 to about 1:3, from about 3:2.5 to about 1:3, from about 3:1 to about 1:2.5, from about 3:1 to about 1:2, from about 3:1 to about 1:1.5, from about 2.5:1 to about 1:3, from about 2:1 to about 1:3, from about 1.5:1 to about 1:3 etc.).

In the present disclosure, a molar ratio between the first hydrogel forming polymer derivative and the second hydrogel forming polymer derivative in the composition may be from about 10:1 to about 1:10 (e.g. from about 10:1 to about 1:10, from about 8:1 to about 1:10, from about 6:1 to about 1:10, from about 5:1 to about 1:10, from about 4:1 to about 1:10, from about 3:1 to about 1:10, from about 2:1 to about 1:10, from about 1.75:1 to about 1:10, from about 1.5:1 to about 1:10, from about 1.25:1 to about 1:10, from about 1:1 to about 1:10, from about 1:1.25 to about 1:10, from about 1:1.5 to about 1:10, from about 1:1.75 to about 1:10, from about 1:2 to about 1:10, from about 1:3 to about 1:10, from about 1:4 to about 1:10, from about 1:5 to about 1:10, from about 6:1 to about 1:6, from about 5:1 to about 1:5, from about 4:1 to about 1:4, from about 3:1 to about 1:3, from about 2:1 to about 1:2, from about 1.75:1 to about 1:1.75, from about 1.5:1 to about 1:1.5, from about 1.25:1 to about 1:1.25, or from about 1.1:1 to about 1:1.1, etc.).

In the present disclosure, a volume ratio between the first hydrogel forming polymer derivative and the second hydrogel forming polymer derivative in the composition may be from about 3:1 to about 1:3 (e.g. from about 3:1 to about 1:3, from about 3:1.5 to about 1:3, from about 3:2 to about 1:3, from about 3:2.5 to about 1:3, from about 3:1 to about 1:2.5, from about 3:1 to about 1:2, from about 3:1 to about 1:1.5, from about 2.5:1 to about 1:3, from about 2:1 to about 1:3, from about 1.5:1 to about 1:3 etc.).

In the present disclosure, the first hydrogel forming polymer derivative may have a first DM, the second hydrogel forming polymer derivative may have a second DM, and a ratio between the first DM and the second DM may be from about 3:1 to about 1:3 (e.g. from about 3:1 to about 1:3, from about 3:1.5 to about 1:3, from about 3:2 to about 1:3, from about 3:2.5 to about 1:3, from about 3:1 to about 1:2.5, from about 3:1 to about 1:2, from about 3:1 to about 1:1.5, from about 2.5:1 to about 1:3, from about 2:1 to about 1:3, from about 1.5:1 to about 1:3 etc.).

In some cases, the first modification and the second modification may be each independently selected from the group consisting of an acrylate, a methacrylate, a maleimide, a vinylsulfone, a thiol, an amine, and any combinations thereof.

In the present disclosure, the first hydrogel forming polymer derivative may be a dextran derivative modified with one or more vinylsulfone groups, a hyaluronic acid derivative modified with one or more vinylsulfone groups, a polyethylene glycol derivative modified with one or more vinylsulfone groups, or a combination thereof, the second hydrogel forming polymer derivative may be a dextran derivative modified with one or more thiol groups, a hyaluronic acid derivative modified with one or more thiol groups, a polyethylene glycol derivative modified with one or more thiol groups, or a combination thereof.

In some cases, the first hydrogel forming polymer derivative and/or the second hydrogel forming polymer derivative may comprise the degradable backbone.

In the present disclosure, the hydrogel forming polymer may have a weight averaged molecular weight from about 10 kDa to about 500 kDa (e.g. from about 10 kDa to about 500 kDa, from about 50 kDa to about 500 kDa, from about 100 kDa to about 500 kDa, from about 150 kDa to about 500 kDa, from about 200 kDa to about 500 kDa, from about 250 kDa to about 500 kDa, from about 300 kDa to about 500 kDa, from about 350 kDa to about 500 kDa, from about 400 kDa to about 500 kDa, from about 450 kDa to about 500 kDa).

In some cases, the composition may be a powder.

In some cases, the composition may be a liquid composition, and a concentration of the one or more hydrogel forming polymers in the liquid composition is from about 10% w/v to about 40% w/v (e.g. from about 10% w/v to about 40% w/v., from about 15% w/v to about 40% w/v., from about 20% w/v to about 40% w/v., from about 25% w/v to about 40% w/v., from about 30% w/v to about 40% w/v., from about 35% w/v to about 40% w/v., from about 38% w/v to about 40% w/v., etc.).

In the present disclosure, the hydrogel forming polymer comprising the degradable backbone may have a polydispersity of 4 or less (e.g. 4, 3, 2, 1, 0.5 or less).

In the present disclosure, the hydrogel forming polymer comprising the degradable backbone may be formed by crosslinking the precursor polymers with the degradable linker, and the degradable linker may enable formation of degradable linkage between the precursor polymers.

In some cases, the precursor polymer may be hydrophilic and/or water soluble.

In some cases, the precursor polymer may be non-hydrolysable, enzymatically non-degradable, or otherwise non-cleavable. For example, when the degradable linker was degraded by hydrolyze, enzyme and other clear pathways, the precursor polymer may not be affected and may maintain the structure of the degradable backbone.

In the present disclosure, the precursor polymer may be selected from the group consisting of a polysaccharide, a polyethylene glycol, a derivative thereof, and any combinations thereof.

In some cases, the precursor polymer may be selected from the group consisting of a dextran, a hyaluronic acid, a polyethylene glycol, a derivative thereof, and any combinations thereof.

In the present disclosure, the precursor polymer may be a derivative comprising one or more (e.g. one, two, three, four, five, six, seven, eight, nine, ten or more) modifications, and a degree of modification of the precursor polymer is less than about 20% (e.g. less than about 20%, less than about 18%, less than about 16%, less than about 14%, less than about 12%, less than about 10%, less than about 8%, less than about 6%, less than about 4%, less than about 2%, less than about 1% or less).

In the present disclosure, the composition for forming the hydrogel forming polymer comprising the degradable backbone, a molar ratio between the degradable linker and the modification on the precursor polymer may be from about 1:1 to about 1:10 (e.g. from about 1:1 to about 1:10, from about 1:2 to about 1:10, from about 1:3 to about 1:10, from about 1:4 to about 1:10, from about 1:5 to about 1:10, from about 1:6 to about 1:10, from about 1:7 to about 1:10, from about 1:8 to about 1:10, from about 1:9 to about 1:10, etc.).

In the present disclosure, the composition for forming the hydrogel forming polymer comprising the degradable backbone, an amount of the degradable linker may be equivalent to crosslinking about 1-5 (e.g. about 1, 2, 3, 4, 5, etc.) the modification per the precursor polymer.

In the present disclosure, the modification of the precursor polymer may be selected from the group consisting of an acrylate, a methacrylate, a maleimide, a vinylsulfone, a thiol, an amine, and any combinations thereof.

In the present disclosure, the degradable linker may comprise two or more (e.g. two, three, four, five, six, seven, eight, nine, ten or more) modifications, and a degree of modification of the degradable linker is less than about 30% (e.g. less than about 30%, less than about 25%, less than about 20%, less than about 15%, less than about 10%, less than about 5%, less than about 1% or less).

In the present disclosure, the modification of the degradable linker may be selected from the group consisting of an acrylate, a methacrylate, a maleimide, a vinylsulfone, a thiol, an amine, and any combinations thereof.

In the present disclosure, the precursor polymer may be a dextran derivative modified with one or more vinylsulfone groups, a hyaluronic acid derivative modified with one or more vinylsulfone groups, a polyethylene glycol derivative modified with one or more (e.g. one, two, three, four, five, six, seven, eight, nine, ten or more) vinylsulfone groups, or a combination thereof, and the degradable linker comprises two or more (e.g. two, three, four, five, six, seven, eight, nine, ten or more) thiol group modifications. For example, the vinylsulfone groups may have a functional group of

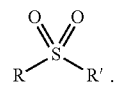

In some cases, the precursor polymer may be a dextran derivative modified with one or more thiol groups, a hyaluronic acid derivative modified with one or more (e.g. one, two, three, four, five, six, seven, eight, nine, ten or more) thiol groups, a polyethylene glycol derivative modified with one or more (e.g. one, two, three, four, five, six, seven, eight, nine, ten or more) thiol groups, or a combination thereof, and the degradable linker comprises two or more (e.g. two, three, four, five, six, seven, eight, nine, ten or more) vinylsulfone group modifications.

In the present disclosure, the degradable linker may be selected from a divinyl methacrylate, a divinyl acrylate, and a derivative thereof.

In some cases, the degradable linker may be selected form the following groups:

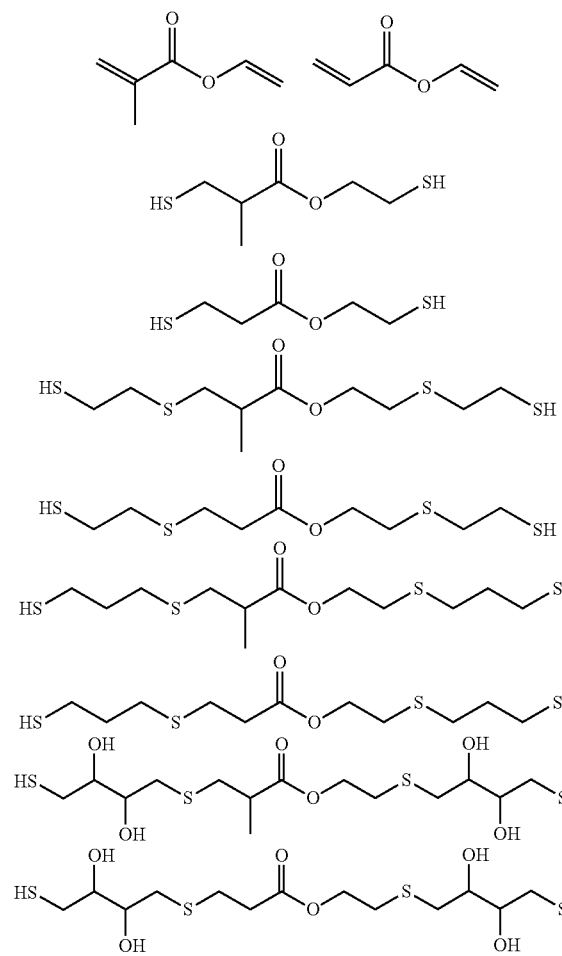

In the present disclosure, the degradable linker may comprise a modulator, an ester. In some cases, the degradable linker may further comprise a linker. In some cases, said ester may be modified with said modulator. For example, one side of said ester may be modified with said modulator, or, both two sides of said ester may be modifies with said modulator. In some cases, the degradable linker having said ester modified on both sides with said modulator may be significantly more stabilized than the degradable linker having said ester modified on one side with said modulator. In some cases, the degradable linker having said ester modified on both sides with said modulator may show a slower ester hydrolysis rate than the degradable linker having said ester modified on one side with said modulator.

Figure 17:
FIG. 17 illustrates a format of the degradable linker.

In some cases, the degradable linker may comprise a modulator, an ester, and a linker. For example, the degradable linker may comprise the format shown in FIG. 17.

In some cases, the two modulators may be the same or be the different. In some cases, the two modulators may be the same.

In some cases, said ester may be selected form the following groups:

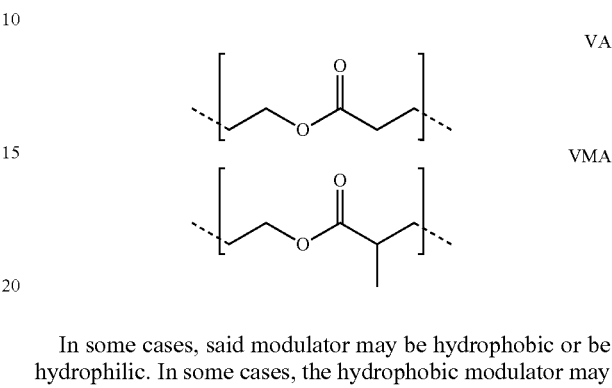

In some cases, said modulator may be hydrophobic or be hydrophilic. In some cases, the hydrophobic modulator may more facilitate the stability of the degradable linker than the hydrophilic modulator. In some cases, the hydrophobic modulator may reduce the solubility of the degradable linker in the aqueous environment.

In some cases, said modulator may be selected form the following groups:

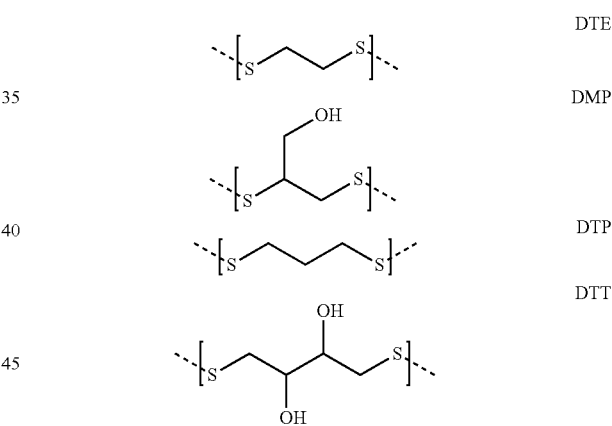

In some cases, said linker may be selected form the following groups:

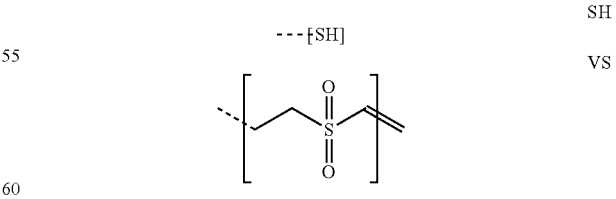

In the present disclosure, the precursor polymer may have a weight averaged molecular weight of 2 kDa to 20 kDa (e.g., 2 kDa, 4 kDa, 6 kDa, 8 kDa, 10 kDa, 12 kDa, 14 kDa, 16 kDa, 18 kDa, 20 kDa, etc.).

In some cases, the molecular weight of the precursor polymer may have an influence on the hydrolytic degradation of the hydrogel forming polymer. For example. the molecular weight of the precursor polymer may be under 100 kDa to achieve a relatively low viscosity even at a relatively high concentration of the precursor polymer.

In some cases, the concentration of the precursor polymer may have an influence on the hydrolytic degradation of the hydrogel forming polymer.

In some cases, the average degree of modification (DM) of the hydrogel forming polymer (e.g. the precursor polymer) may have an influence on the hydrolytic degradation of the hydrogel forming polymer.

In some cases, the degradable backbone may maintain good solubility in aqueous environment.

In another aspect, the present disclosure provides a hydrogel for sustained release of a target agent, wherein the hydrogel may be formed with the composition.

Figure 18:
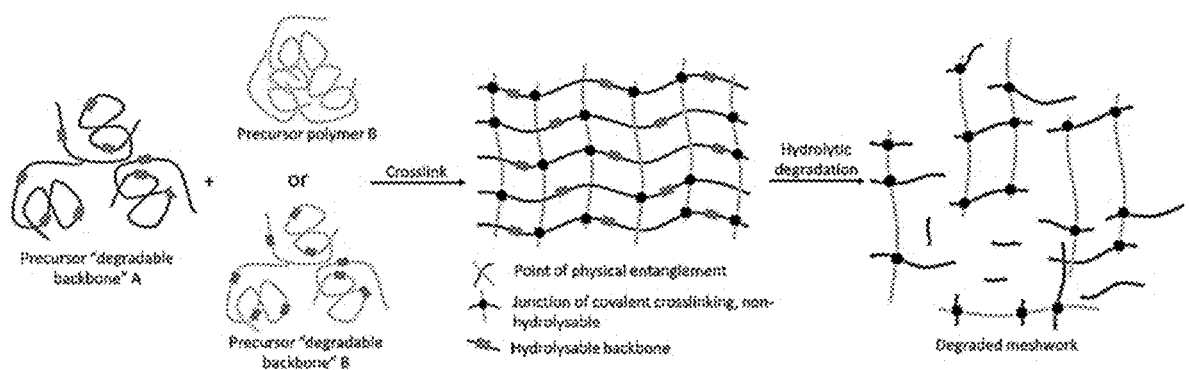
FIG. 18 illustrates the formation and degradation of the hydrogel.

In the present disclosure, the hydrogel may disassociate as the precursor polymer got cleaved. In some cases, the molecular weight of degradation products of the hydrogel may span over a wide range of values. The formation and degradation of the hydrogel may be shown in FIG. 18.

In the present disclosure, the hydrogel may also have many other advantages, such as having a lower viscosity, adjusted speed of degradation which is slower than that of a corresponding junction-lysable hydrogel.

Figure 13:
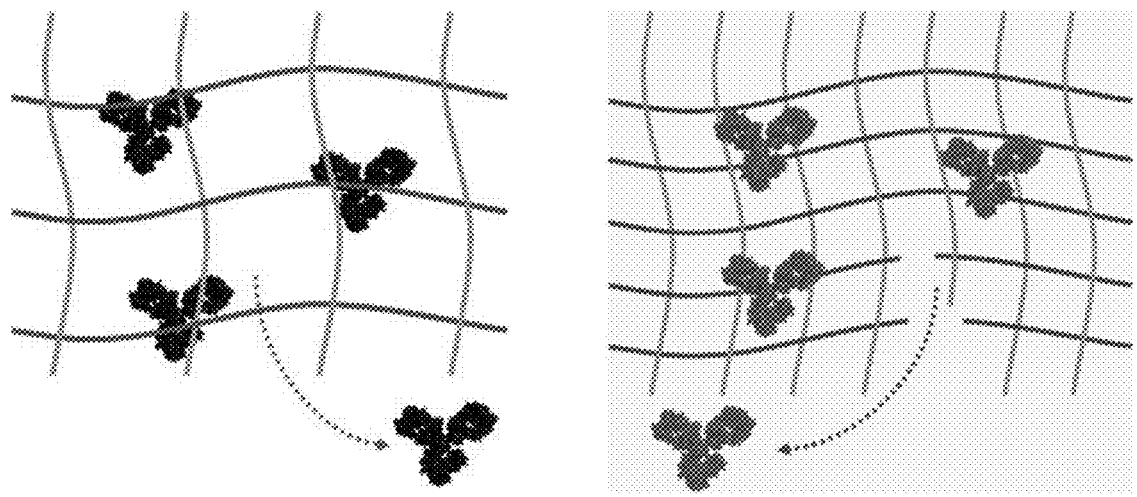
FIG. 13 illustrates release of proteins from hydrogel meshwork controlled by different meshwork.

In the present disclosure, the release of proteins from hydrogel meshwork controlled by different meshwork can be illustrated in FIG. 13.

In the present disclosure, the hydrogel further may comprise the target agent.

In some cases, the target agent comprises a macromolecule. For example, the target agent may comprise a protein or a polypeptide.

In the present disclosure, about less than 30% (e.g. less than about 30%, less than about 25%, less than about 20%, less than about 15%, less than about 10%, less than about 5%, less than about 1% or less) of the target agent may be cumulatively released within an initial 24 hours (e.g. within an initial 24 hours, 22 hours, 20 hours, 18 hours, 16 hours, 14 hours, 12 hours, 10 hours, 8 hours, 6 hours, 4 hours, 2 hours or less) from the hydrogel, and the remaining portion of the target agent may be cumulatively released from the hydrogel in about 3 to about 36 months (e.g. about 3 to about 36 months, about 4 to about 36 months, about 5 to about 36 months, about 6 to about 36 months, about 7 to about 36 months, about 8 to about 36 months, about 9 to about 36 months, about 10 to about 36 months, about 12 to about 36 months, about 14 to about 36 months, about 16 to about 36 months, about 18 to about 36 months, about 18 to about 24 months, about 20 to about 24 months, about 22 to about 24 months).

In the present disclosure, the initial 24 hours (e.g. within an initial 24 hours, 22 hours, 20 hours, 18 hours, 16 hours, 14 hours, 12 hours, 10 hours, 8 hours, 6 hours, 4 hours, 2 hours or less) may be started to timing once the hydrogel containing the target agent is formed.

Figure 15:
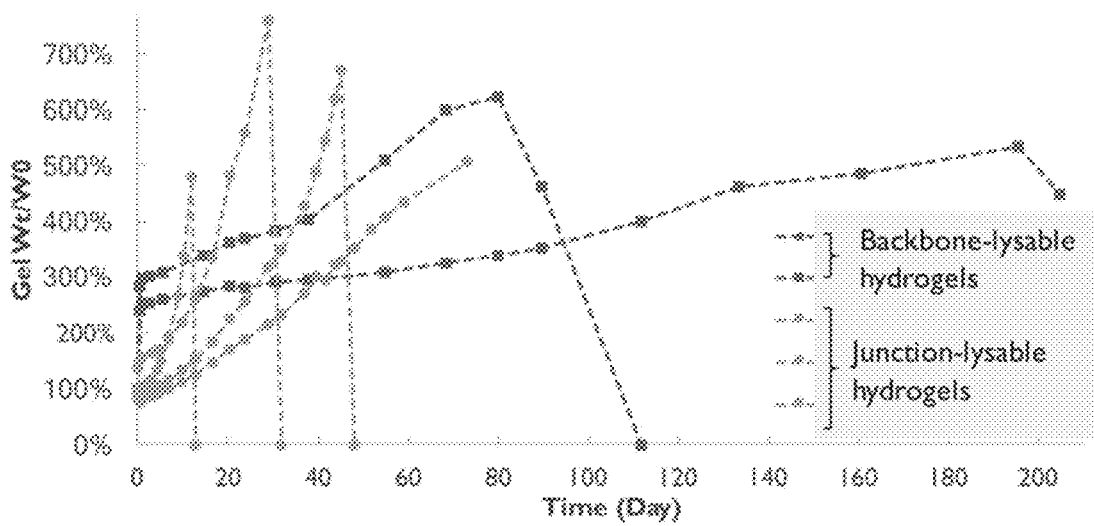
FIG. 15 illustrates a stability of backbone-lysable hydrogel and junction-lysable hydrogels.

In the present disclosure, the stability or cumulatively released of the hydrogel may be illustrated in FIG. 15.

In another aspect, the present disclosure provides a method for producing a hydrogel, and the method may comprise: a) providing the composition; b) mixing the composition with a buffer to form a polymer solution; and c) subjecting the polymer solution to a condition enabling formation of the hydrogel.

In the present disclosure, the subjecting may comprise injecting the polymer solution in a subject in need thereof.

In some cases, the subjecting may comprise incubating the composition at about 30° ° C. to about 45° C. (e.g., about 30° ° C. to about 45° C., about 31° ° C. to about 45° C., about 32° ° C. to about 45° C., about 33° C. to about 45° C., about 34° ° C. to about 45° C., about 35° C. to about 45° C., about 36° C. to about 45° ° C., about 37° ° C. to about 45° C., about 38° C. to about 45° C., about 39° C. to about 45° C., about 40° ° C. to about 45° C., about 41° ° C. to about 45° C., about 42° C. to about 45° C., about 43° C. to about 45° C., about 44° C. to about 45° C., etc.).

In the present disclosure, the polymer solution further may comprise the target agent.

In another aspect, the present disclosure provides a method for producing the composition may comprise: a) crosslinking the precursor polymer with the degradable linker to obtain the hydrogel forming polymer comprising the degradable backbone; and b) mixing the hydrogel forming polymer comprising the degradable backbone with an additional polymer, wherein the additional polymer is capable of reacting with the hydrogel forming polymer comprising the degradable backbone under a condition enabling formation of the hydrogel.

In another aspect, the present disclosure provides a method for sustained release of a target agent, and the method may comprise: mixing the target agent with a composition to obtain a mixture and subjecting the mixture to a condition enabling formation of a hydrogel capable of sustained release of the target agent.

In another aspect, the present disclosure provides a method for sustained release of a target agent, and the method may comprise enclosing the target agent in the hydrogel.

In some embodiments, the method may comprise incubating the composition at about 30° ° C. to about 45° C. (e.g., at about 32° ° C. to about 40° C., at about 35° C. to about 40° C., such as at about 37° C.).

In another aspect, the present disclosure provides a kit, and the kit may comprise: a) the composition; and b) a target agent to be sustained released by a hydrogel formed with the composition of a).

In some cases, the kit may further comprise one or more of the following: a stabilizer, a bulking agent, a filler, a diluent, an anti-adherent, a binder, a coating agent, a coloring agent, a disintegrant, a flavor, a fragrance, a lubricant, and/or an antioxidant.

In another aspect, the present disclosure provides a use of the composition for making a hydrogel.

In another aspect, the present disclosure provides a use of the composition or the hydrogel for sustained release of a target agent.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

EXAMPLES

The following examples are set forth so as to provide those of ordinary skills in the art with a complete disclosure and description of how to make and use the present invention and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or see, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1 Preparation of Non-Hydrolysable Dextran-VS and Dextran-SH

The vinyl sulfone (VS) and thiol (SH) functionalized dextran, DX-VS and DX-SH were synthesized using previously reported method (refers to Y. Yu and Y. Chau, "One-step 'click' method for generating vinyl sulfone groups on hydroxyl-containing water-soluble polymers," *Biomacromolecules*, vol. 13, pp. 937-942, 2012.). In brief, divinylsulfone (DVS) reacts with hydroxyl groups on dextran in aqueous, alkaline condition to make DX-VS (reaction 1A, FIG. 1A). Thiol functionalized dextran were made in two ways: the first was using dithiothreitol (DTT) to react with the VS groups on DX-VS in phosphate buffered solution to make DX-SH (reaction 1B, FIG. 1B). The products were purified by dialysis in water, and polymers in dried form were prepared by lyophilization. Degree of modification (DM) as was defined $$\frac{\text{No. of pendant groups}}{\text{No. of repeating unit of polymer}}.$$

DM of DX-VS was estimated using $^1$H NMR, and DM of DX-SH was estimated by Ellman's assay.

Example 2 Preparation and Characterization of Dithiol-Ester Linkers

Figure 2:
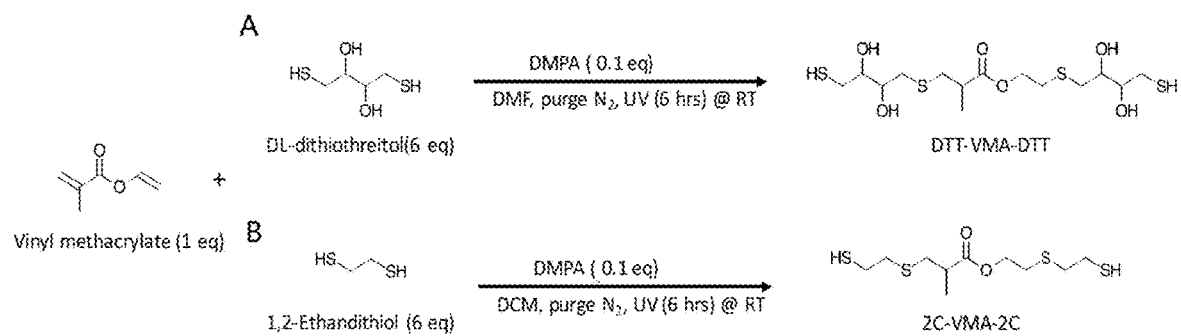
FIG. 2A-2B illustrate synthesis schemes of dithiol-ester linkers.

Two types of dithiol-ester linkers were synthesized by conjugating thiol groups, DL-dithiothreitol (DTT) (FIG. 2A) or 1,2-ethandithiol (FIG. 2B), to both arms of vinyl methacrylate (VMA) were reacted. For DTT conjugation, VMA and DTT were dissolved in dimethylformamide (DMF), 2,2-Dimethoxy-2-phenylacetophenone (DMPA) was added as the radical initiator. The mixture was purged with nitrogen for 30 minutes to exhaust dissolved air in sealed quartz flask. After UV illuminated for six hours, the DTT-VMA-DTT were precipitated with cold ether to remove excess unconjugated DTT. Pellet was resuspended in water, purified by dialysis and lyophilisation.

The conjugation of 1,2-ethandithiol to VMA was carried out in DCM with the same protocol.

With the same protocol, DTP (1,3-propanedithiol) and VMA was reacted to form DTP-VMA-DTP; DTE (1,2-ethanedithiol) and VMA was reacted to form DTE-VMA-DTE; and DTE and VA (vinyl acrylate) was reacted to form DTE-VA-DTE.

The product DTE-VMA-DTE was vacuum dried overnight to vaporize DCM and excess 1,2-ethandithiol. The remaining oil-like liquid was resuspended in DMF, stored at −20° C. upon using. The product dithiol-ester linkers were confirmed by mass spectrum and $^1$H NMR.

Figure 5:
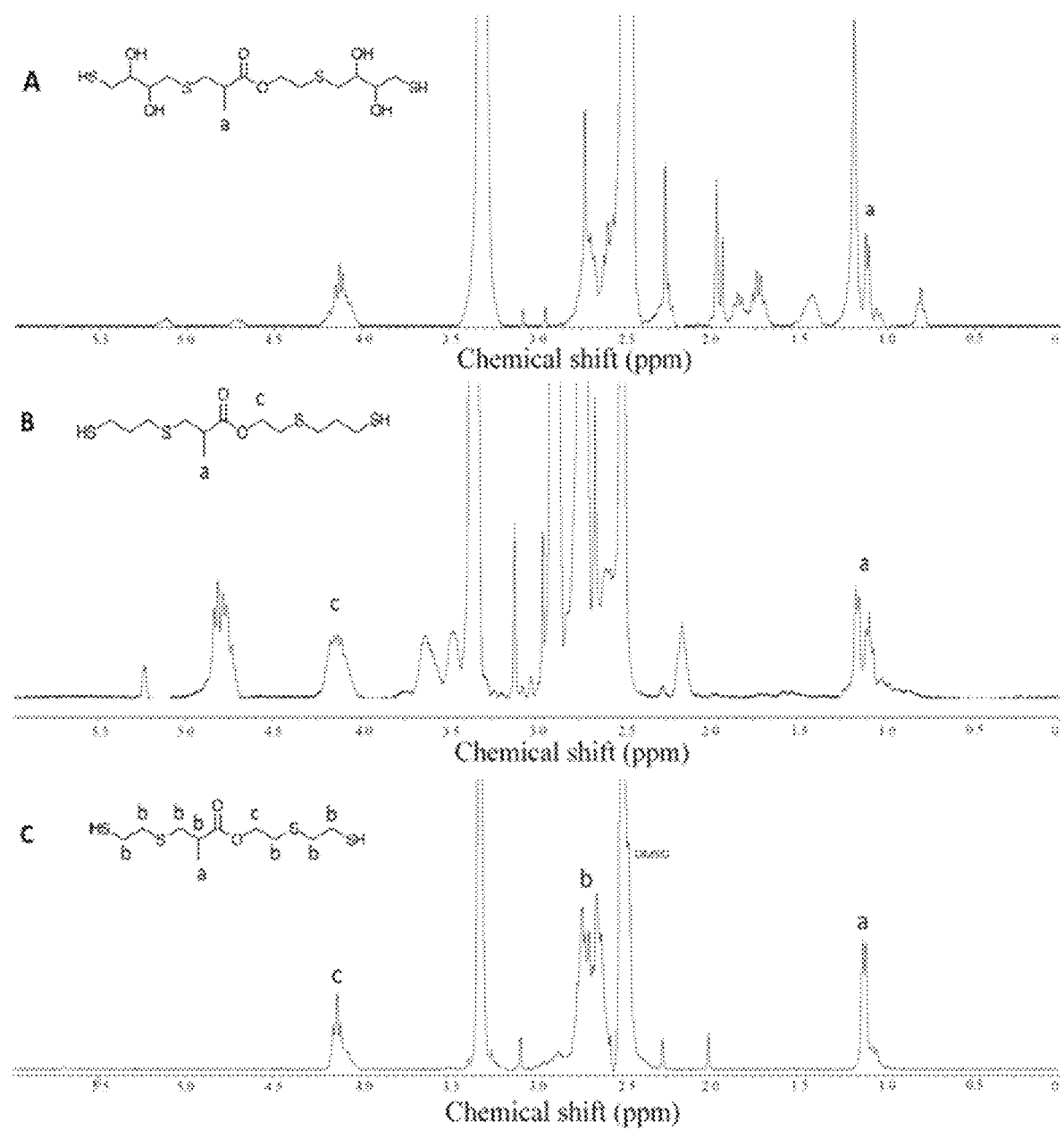
FIG. 5A-5C illustrate the $^1$H-NMR spectra of dithiol-ester linkers.

The $^1$H-NMR spectra of dithiol-ester linkers in DMSO after crude purification is shown in FIG. 5A-5C, wherein FIG. 5A illustrates DTT-VMA-DTT; FIG. 5B illustrates DTP-VMA-DTP; and FIG. 5B illustrates DTE-VMA-DTE.

Example 3 Preparation of Hydrolysable Dextran-O-SH and Dithiol-Ester Crosslinked Dextran-VS

3.1 Preparation of Hydrolysable Dextran-O-SH

Figure 3:
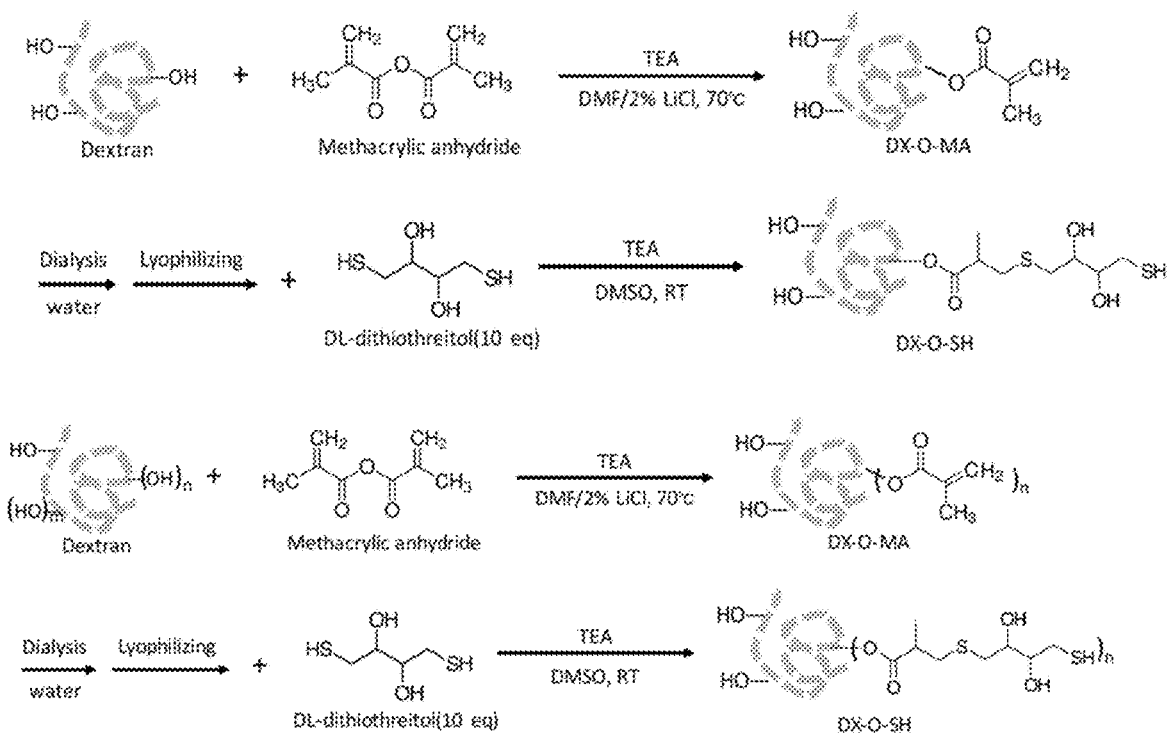
FIG. 3 illustrates synthesis schemes of ester bearing dexrtan (DX-O-SH).

Methacrylate was conjugated to dextran via oxyester linkage according to Kim & Chu's protocol (refers to S. H. Kim and C. C. Chu, "Synthesis and characterization of dextran-methacrylate hydrogels and structural study by SEM.," *J. Biomed. Mater. Res.*, vol. 49, no. 4, pp. 517-27, 2000). Dextran were dissolved in DMF/2% LiCl (5 w/v %) at 90° ° C. oil bath. After dextran was completely dissolved, methacrylate anhydride (MA, 0.3~0.5 eq to hydroxyl groups on dextran) and triethylamine (TEA, 0.01 eq to MA) was added, and resumed to ambient temperature to react for overnight. Intermediate dextran-methacrylate (DX-O-MA) were precipitated in isopropanol, then purified by dialysis in water and lyophilisation. DM of MA was estimated using $^1$H NMR. In the second step, DX-O-MA (5 w/v %) and DTT (6 eq to MA) was dissolved in DMSO at ambient temperature, purged with $N_2$ to eliminate dissolved air. Reaction was catalyzed using TEA (0.5 eq to MA) for overnight. DM of thiol was measured by 1H NMR and Ellman's assay. The synthesis scheme of ester bearing dextran (DX-O-SH) is shown in FIG. 3.

3.2 Features of Vinyl Sulfone and Thiol Functionalized Dextran

The features of polymers prepared in Example 1 and 3 were measured and valued. The results are shown in Table 1. In Table 1, the degree of modification (DM) is defined as the ratio of grafted functional groups to repeating unit per polymer chain.

TABLE 1

| Functionalized dextran | Molecular weight | DM | No. of pedant groups per polymer chain |
|---|---|---|---|
| DX6k-VS_5% | 6 kDa | 5% | 1.7 |
| DX6k-VS_7% | | 7% | 2.6 |
| DX6k-VS_18% | | 18% | 6.7 |
| DX40k-VS_5% | 40 kDa | 5% | 12 |
| DX40k-SH_5% | | 5% | 12 |
| DX40k-O-SH_5% | 40 kDa | 5% | 12 |
| DX40k-O-SH_8% | | 8% | 20 |

3.3 Preparation of Dithiol-Ester Crosslinked Dextran-VS

Figure 4:
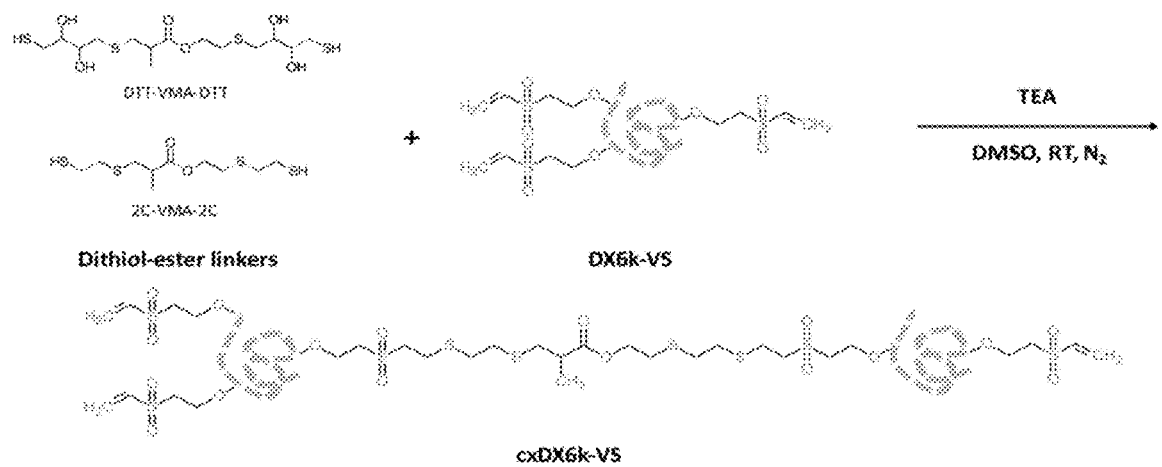
FIG. 4 illustrates synthesis schemes of pre-crosslink of cxDX6k-VS backbone using dithio-lester linkers.

Dithiol-ester linkers were used to crosslink short chain DX6k-VS. DX6k-VS were dissolved in DMSO at 10 w/v %, purged with $N_2$ to eliminate dissolved air. Dithiol-ester linkers prepared in Example 2 were added at the amount that were equivalent to crosslink 1.2~4 VS per DX6k-VS chains (refers to FIG. 4). TEA at 0.125~0.5 eq to VS added as catalyst. The crosslinking reaction was stopped while reactant gave a negative result in Ellman's assay. After crosslinking was completed, CXDX6-VS was precipitated with isopropanol, then purified by dialysis against water, finally lyophilized and stored at −20° C. upon use.

From above, it is indicated that backbone-lysable hydrogels were formulated with two kind of polymer precursors: the pre-crosslinked hydrolysable dextran chains with pedant VS, and the DX40k-SH.

The low molecular weight Dx6k-VS was firstly crosslinked with dithiol-ester linkers to constitute longer chains (abbreviated as cxDX6k-VS). During the crosslinking step, polymer concentration of short chains was kept higher than its theoretical overlapping concentration to promote interchain crosslinking. The feeding ratio of dithiol-ester linkers should be below the amount needed to crosslink 2 VS groups per Dx6k-VS chain. Higher dithiolinker/VS ratio would increase the chance of over-crosslinking, which led to gelation. The remaining free VS groups on cxDX6k-VS species were used for the second-step crosslinking, which was used to crosslink with DX40k-SH to form the polymer network. The name "backbone-lysable" emphasized the feature that hydrolytic cleavage occurs at the esters on the "backbone" of cxDX6k-VS polymers. The junctions between cxDX6k-VS and DX40k-SH were not hydrolysable.

3.4 Comparation of Two Types of Hydrolysable Formulations

Figure 7:
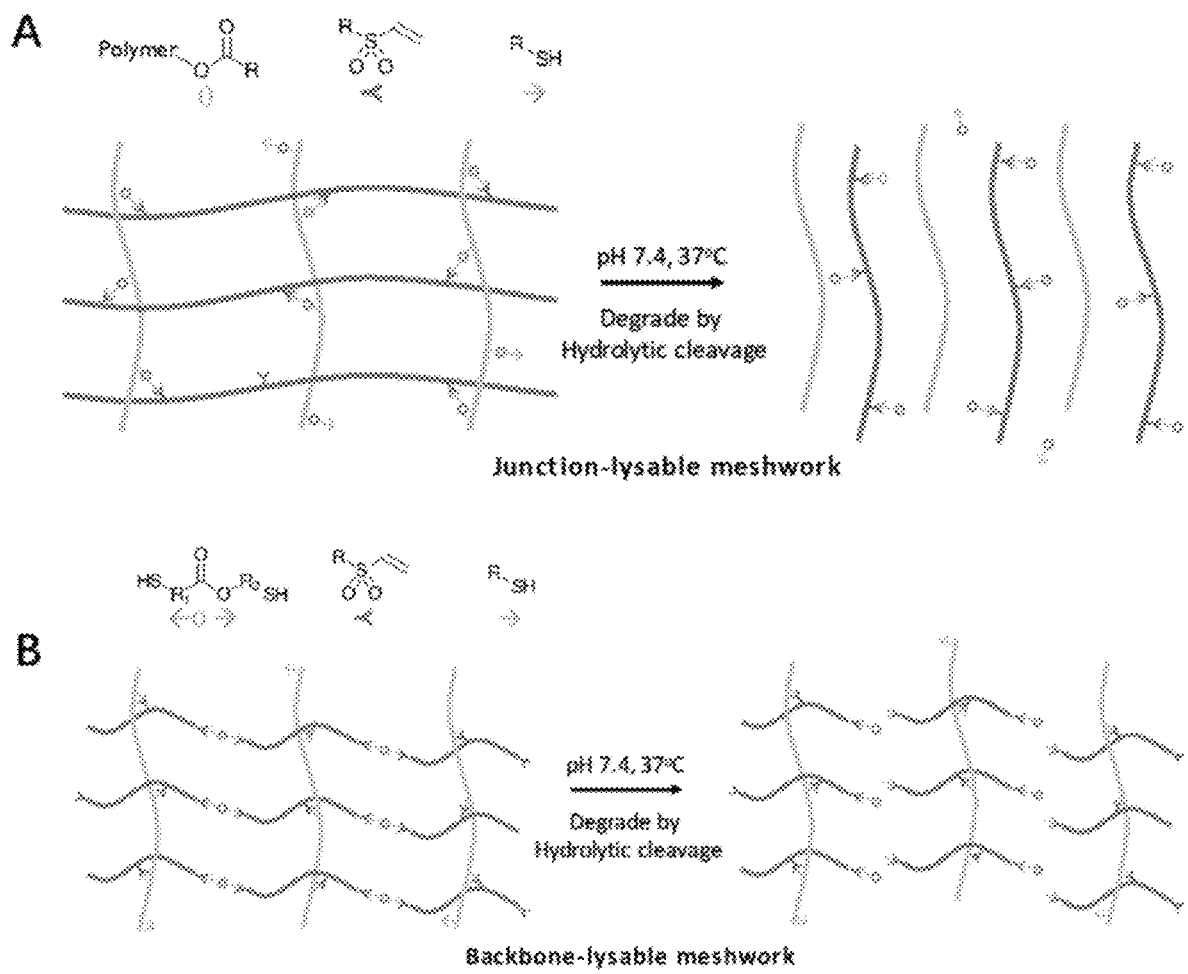
FIG. 7A-7B illustrate two types of hydrolysable formulations: junction-lysable and backbone-lysable hydrogels.

Two types of hydrolysable formulations: junction-lysable and backbone-lysable hydrogels were formulated. The two formulations were distinguished by the placement of the hydrolytic esters (refers to FIG. 7A-7B, 7A illustrates the junction-lysable meshwork while 7B illustrates Backbone-lysable meshwork). In junction-lysable formulations, the esters were placed in between the polymer chain and the thiols (abbreviated as DX-O-SH), so that every crosslinking junction was hydrolysable. Due to the simplicity of synthesis, this strategy that places cleavable groups between crosslinking junctions between polymers, is the most common way of forming degradable hydrogels. The degradation product after complete hydrolysis would have the similar molecular weight as the precursor polymers.

Example 4 Hydrogel Degradation by Ester Hydrolysis

Hydrogel Casting

DX-VS, or cxDX-VS were dissolved in pH 7.4, 0.1M phosphate buffer, or pH adjusted IgG solutions (pH 7.4) at desired concentration. DX-O-SH/DX-SH were dissolved in water. Two precursor polymer solutions were mixed thoroughly at 4° C., and then being pipetted on a hydrophobic surface as hemispherical droplet. The polymer solution droplets were incubated in a humid chamber at ambient temperature for overnight, or at 37° C. for 1 hour to allow gelation.

Measuring Hydrolysis Rate of Esters in Hydrogel by Mass Swelling Test

Then the hydrogels were incubated pH 7.4 PBS/0.02 w/v % NaNa at 37° C. Hydrogel wet weight at various time points were measured. The surface liquid on hydrogels was carefully drained dried with tissue paper. The collapsing time was defined as the time when the hydrogel was too weak to handle.

Hydrogel Degradation by Ester Hydrolysis

Figure 6:
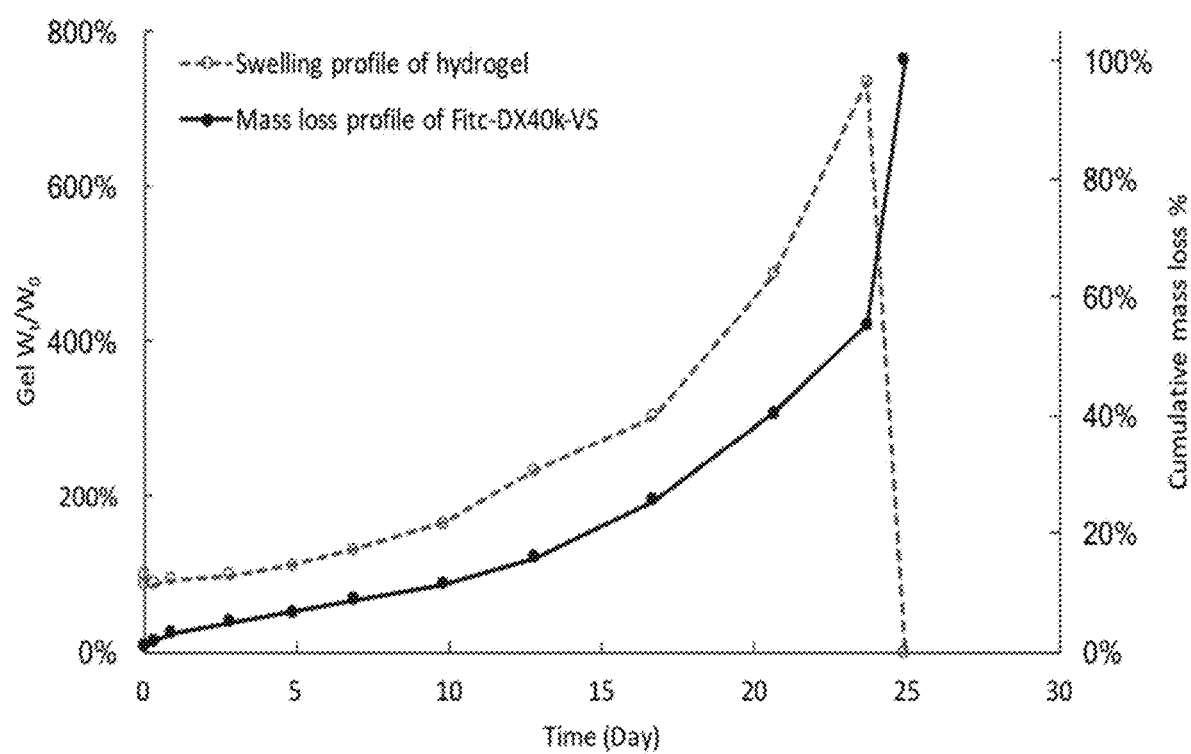
FIG. 6 illustrates representative swelling profile of junction-lysable hydrogel and it corresponding polymer mass loss profile of Fitc labeled DX40 kDa-VS over time.

In vitro degradation of hydrolysable formulations was measured using the swelling profile. The precursor polymers were functionalized with -VS and -SH respectively. The -VS and -SH groups crosslink the polymers via Michael addition and form a network. The hydrogel swelling ratio was defined as the wet weight at time t ($W_t$) over the wet weight at relax state ($W_0$). Once the hydrogels are immersed in excess buffer, hydrogels at relax state may swell, or shrink until equilibrium state is reached. The swelling ratio of hydrogel constituted with a specific polymer (dextran was used in this study) is temperature and solvent dependent. For dextran-based hydrogels in PBS (pH 7.4) at 37° C., the equilibrating process empirically take 24-48 hours to complete. During the process, the unreacted -VS and —SH groups, which were not co-localized at entanglement points at relax state may have the chance to react and form new crosslinks. The crosslinking density of a hydrogel reached maximum at its equilibrium state. Without further crosslinking nor degradation, the swelling ratio would be steady then. If there was further crosslinking, for example the disulfide crosslinking between unreacted thiol groups, the swelling ratio would decrease. The degradable hydrogels would initially swell gradually, and collapse in the later stage. Assuming all esters share the same hydrolysis rate, the cleavage of junctions is random and independent of its location on the polymer network. In the early stage of degradation, most polymers are still covalently crosslinked as a continuous network, and only a small fraction of polymers that detached from the network could escape by diffusion and reptation. While the gel weight loss due to polymer escape was smaller than gel weight gains due to water molecule influx, the hydrogel swells was observed (FIG. 6). In the later stage of degradation, significant fraction of polymers starts to detach, the hydrogel would lose its integrity and quickly disintegrate into fragments.

FIG. 6 illustrates representative swelling profile of junction-lysable hydrogel in PBS at 37° C., and it corresponding polymer mass loss profile of Fitc labelled DX40 kDa-VS over time. Among them, Fitc-DX40k-VS (conc. 10%/DM 9%) was crosslinked with DX40k-O-SH (conc. 20%/DM 8%).

Example 5 Hydrolysis of Hydrogels Effected by Various Hydrogel Parameters

Figure 8:
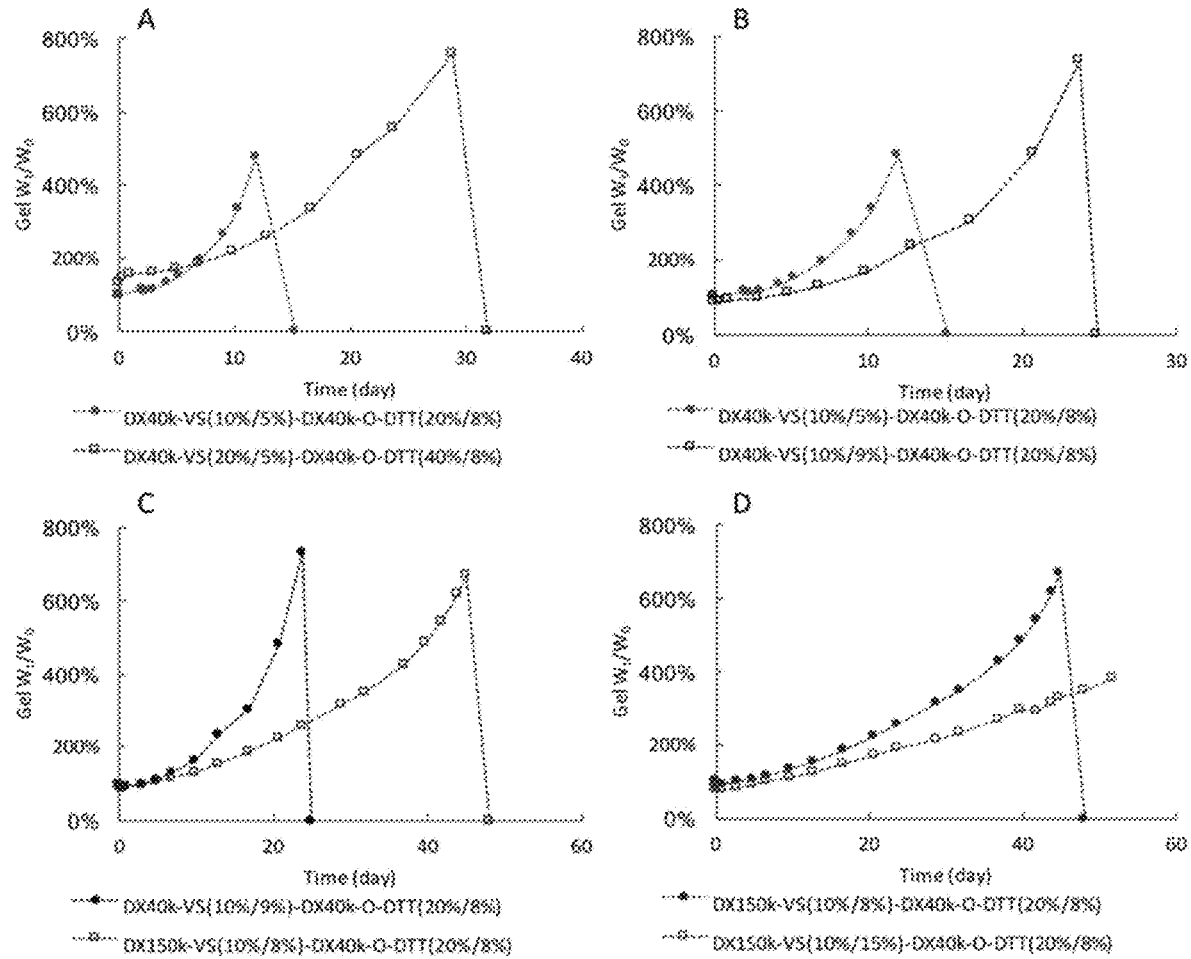
FIG. 8A-8D illustrate impact of polymer concentration, degree of modification, molecular weight of polymers on linkage hydrolysis induced hydrogel swelling profile.

Junction-lysable hydrogels were used to demonstrate the effect of various hydrogel parameters, such as polymer concentration, degree of modification (DM) and polymer molecular weight on degradation kinetics. In general, the time required for a hydrogel to disintegrate correlates with DM, polymer concentration, and molecular weight. When DM and molecular weight were fixed, formulations with higher initial polymer concentration required longer time for the hydrogel network to disintegrate (FIG. 8A). While keeping polymer concentration and molecular weight fixed, higher DM prolonged the gel disintegration time (FIG. 8B, FIG. 8D). Hydrogels formulated using precursor polymers with higher molecular weight had longer time disintegration time (FIG. 8C). A mathematic model correlated the junction cleavage at microscopic level to the measureable swelling behavior of hydrogels at macroscopic level was reported to describe the stochastic degradation (refers to G. Jahanmir, M. J. Abdekhodaie, and Y. Chau, "Stochastic Modeling of Degradation Behavior of Hydrogels," *Macromolecules, vol. 51, no. 11, pp. 3941-3952, June 2018*). By inputting the initial structural parameters including the solvent-polymer interaction parameters, molecular weight and polymer concentration of precursor polymers, DM of cleavable crosslinkers, as well as the cleavage rate constant, the model gives a quantitative prediction of the swelling profile and the disintegration time of hydrogels.

In FIG. 8A-8D, the various factors (polymer concentration, degree of modification, molecular weight of polymers) impacting on linkage hydrolysis induced hydrogel swelling profile were measured in PBS at 37° C. The parameters are presented in captions as (polymer concentration/degree of modification). Error bars were omitted for visual clarity.

Example 6 Hydrolysis of Hydrogel Effected by Various Linker

Figure 9:
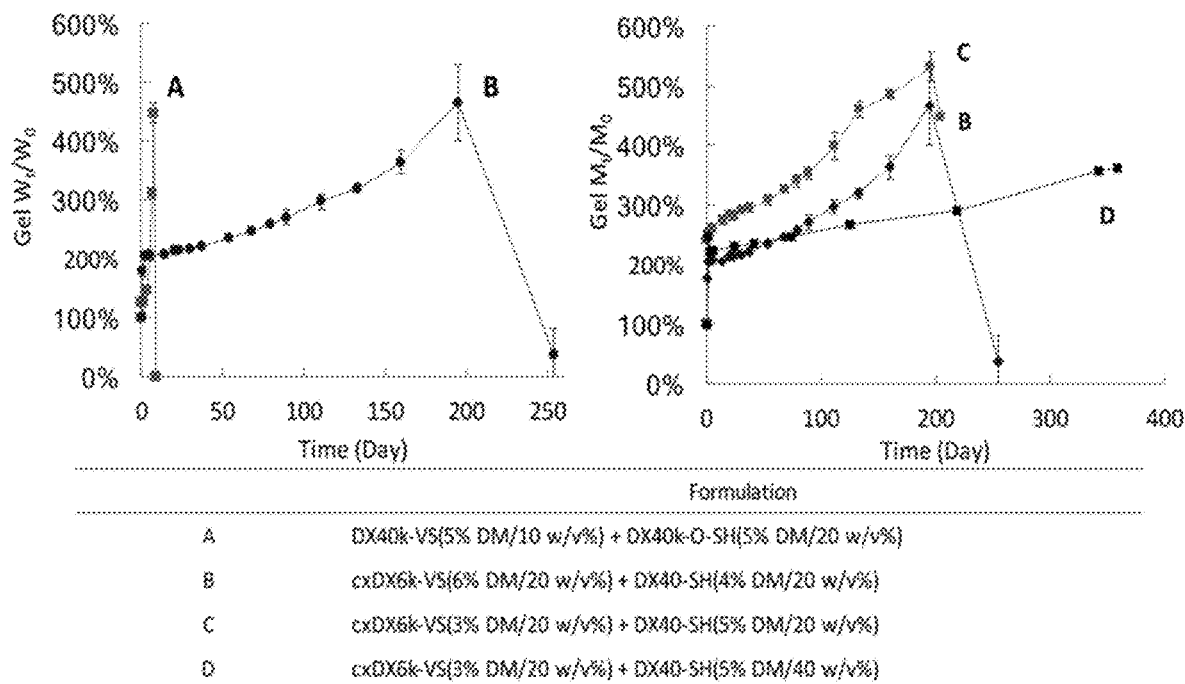
FIG. 9 illustrates the degradation profile of junction-lysable and backbone-lysable hydrogels.

Two type of dithiol-ester linkers (DTT-VMA-DTT and DTE-VMA-DTE) were synthesized. These two linkers were expected to exhibit different hydrolysis rates. The DTT-VMA-DTT linker was designed to mimic the chemical structure of the ester consisting linkage in junction-lysable hydrogels. It was unexpected that the backbone-lysable hydrogels degraded much slower than the junction-lysable counterparts (FIG. 9). Due to the similarity of ester chemical structure, we attribute the difference in degradation rate to other factors. The structure of backbone-lysable network indeed mimicked a junction-lysable network that was cross-linked with polymers of very large molecular weight (hundreds of kDa), but at relatively low cleavable crosslinking density. However, the hydrogel precursor polymers had relatively much lower molecular weight before gelation, which led to much lower viscosity so that the in situ forming hydrogel was practically easy to inject.

FIG. 9 illustrates the degradation profile of junction-lysable and backbone-lysable hydrogels at pH 7.4, 37° C. Formulations are presented as (polymer concentration/degree of modification). Error bars represent one SD from the mean.

Example 7 Release of Model Protein (IgG) from Hydrogels

Measuring Protein Release from Degradable Hydrogel Depot

FITC labelled IgG (F-IgG, 150 kDa) and bevacizumab (150 kDa) were released as model protein. Model protein laden hydrogels were incubated in pH 7.4 PBS/0.02 w/v % $NaN_3$ at 37° C. New release buffer was changed at every sampling time points. Hydrogel released F-IgG were measured by spectrophotometry at 490/520 nm excitation/emission. The fluorescence intensity-concentration standard curves of F-IgG were established at pH 4.5 and pH 7.4. Concentration of bevacizumab was measured by Bradford assay.

Controlling the relative pore/drug size ratio is a commonly used strategy to control the release of macromolecules from hydrogels. Hydrogel laden protein molecules diffuse in the aqueous phase through the polymer network. Mesh size, which is defined as the distance between neighbouring crosslinks, is a parameter that correlates the pore size in hydrogels. In a previous report, we applied De Gennes' blob theory to approximate the average mesh size in chemically crosslinked polymer-polymer hydrogels (refers to Y. Yu and Y. Chau, "Formulation of In Situ Chemically Cross-Linked Hydrogel Depots for Protein Release: From the Blob Model Perspective," *Biomacromolecules*, vol. 16, no. 1, pp. 56-65, January 2015), using the equation:

$$\xi_m \approx Q_r^{1/3} R_g \left(\frac{c}{c^*}\right)^{-\frac{v}{3v-1}}, \quad \text{(Equation 1)}$$

wherein $Q_r$ is the swelling ratio of hydrogels from relax state to equilibrium state; $R_g$ is the radius of gyration of polymer; c and c* are the concentration and overlapping concentration of the polymer respectively; v is the Flory polymer-solvent interaction parameter. It should be noted the mesh size calculated using this model is the mean value, the distribution of meshes in the system is not considered. Also, the value of estimated mesh size is only an indication of, but not equal to the real pore size in the "meshwork". This estimation method provides a quick tool guiding the rational formulation design.

Release of Model Protein (IgG) from Non-Degradable Hydrogels

Figure 10:
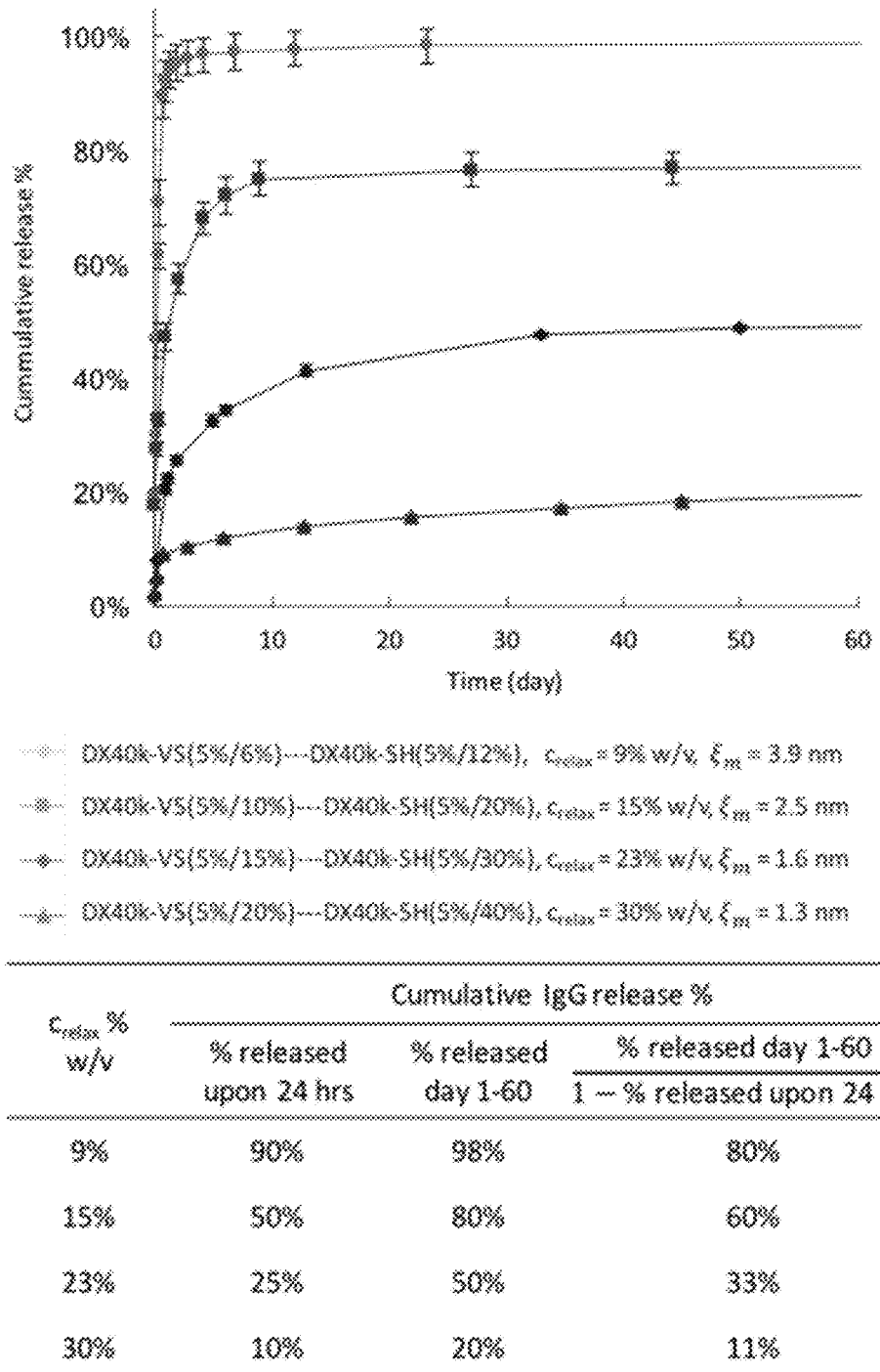
FIG. 10 illustrates cumulative fractional release of IgG from non-degradable dextran based hydrogel formulations varied in initial polymer concentrations.

FIG. 10 demonstrated the release profile of IgG (150 kDa) from various non-degradable dextran based hydrogels, with different initial polymer concentrations. As we aim to control the protein release merely by meshwork based physical hindrance, the molar ratio of SH to VS was kept in two-fold excess to maximize the crosslinking with VS groups, as free -VS can immobilize laden IgG via binding to amines, although at a slower rate.

While the DM of molecular weight of precursor polymers (DX40k-VS and DX40k-SH) were fixed, polymer concentration at relax state affected the release rate, fraction loss due to initial burst and sustained released portion of laden IgG. In the application, the "initial burst" was defined as the IgG fraction being released in first 24 hours. As previously mentioned, the dextran based hydrogels crosslinked via VS-SH addition required 24 to 48 hours to reach equilibrium state. During this process, a hydrogel would experience certain degree of swelling or shrinkage, then reached the equilibrium state. The transport of laden protein during this dynamic period is out of the scope of this study and will be discussed in a separate manuscript. Reducing average mesh size was effective to suppress the initial burst (FIG. 10). As polymer concentration increased from 9% to 30% w/v, the bust released fraction was suppressed from 90% down to 10%. On the other hand, smaller mesh size also correlated with slower IgG release rate. Considering the hydrogel laden IgG molecules were randomly distributed in a stochastic polymer network, a single diffusion coefficient cannot describe the IgG movement in the meshwork. The curved IgG release trend line (FIG. 10) also indicated that the meshwork laden IgG molecules had a mixed diffusion coefficients. Therefore, we compared the "sustained released" fraction, which was defined as the ratio of cumulative IgG fraction released in from day 1 to day 60 to the amount left in the meshwork after initial burst. While polymer concentration was increased from 9 w/v % to 30 w/v %, the "sustained released" fraction decreased from 80% to only 11%. Most of the IgG was trapped inside the 30 w/v % hydrogel.

FIG. 10 illustrates cumulative fractional release of IgG (pH 7.4, 37° C.) from non-degradable dextran based hydrogel formulations varied in initial polymer concentrations. Hydrogel formulations are presented as (DM/polymer concentration). $c_{relax}$ is the polymer concentration in hydrogels at relax state. $\xi_m$ is the approximated mesh size using equation 1. Error bars represent one SD from the mean. The IgG fraction being released from different formulations after 24 hrs and 60 days are listed on the right.

The IgG release data obtained from non-degradable hydrogels revealed a dilemma in formulation design, especially for those aimed for controlled release over multiple months. Smaller mesh size is favored for lowering the initial burst, but the tradeoff would be incomplete release. On the other hand, complete release could be achieved by enlarging mesh size, but most of the laden IgG were not released in a controlled manner. In light of such limitations, meshwork degradation was utilized to complement the mesh controlled, diffusion driven release of proteins from the hydrogel depots. For example, about 80% of IgG was trapped in the 30% w/v non-degradable hydrogel. It is hypothesized that by controlling the rate of mesh opening, the immobilized IgG molecules could be released, and the release rate would be a function of degradation rate.

Example 8 Release of Model Protein (IgG) from Hydrolysable Hydrogels

Figure 11:
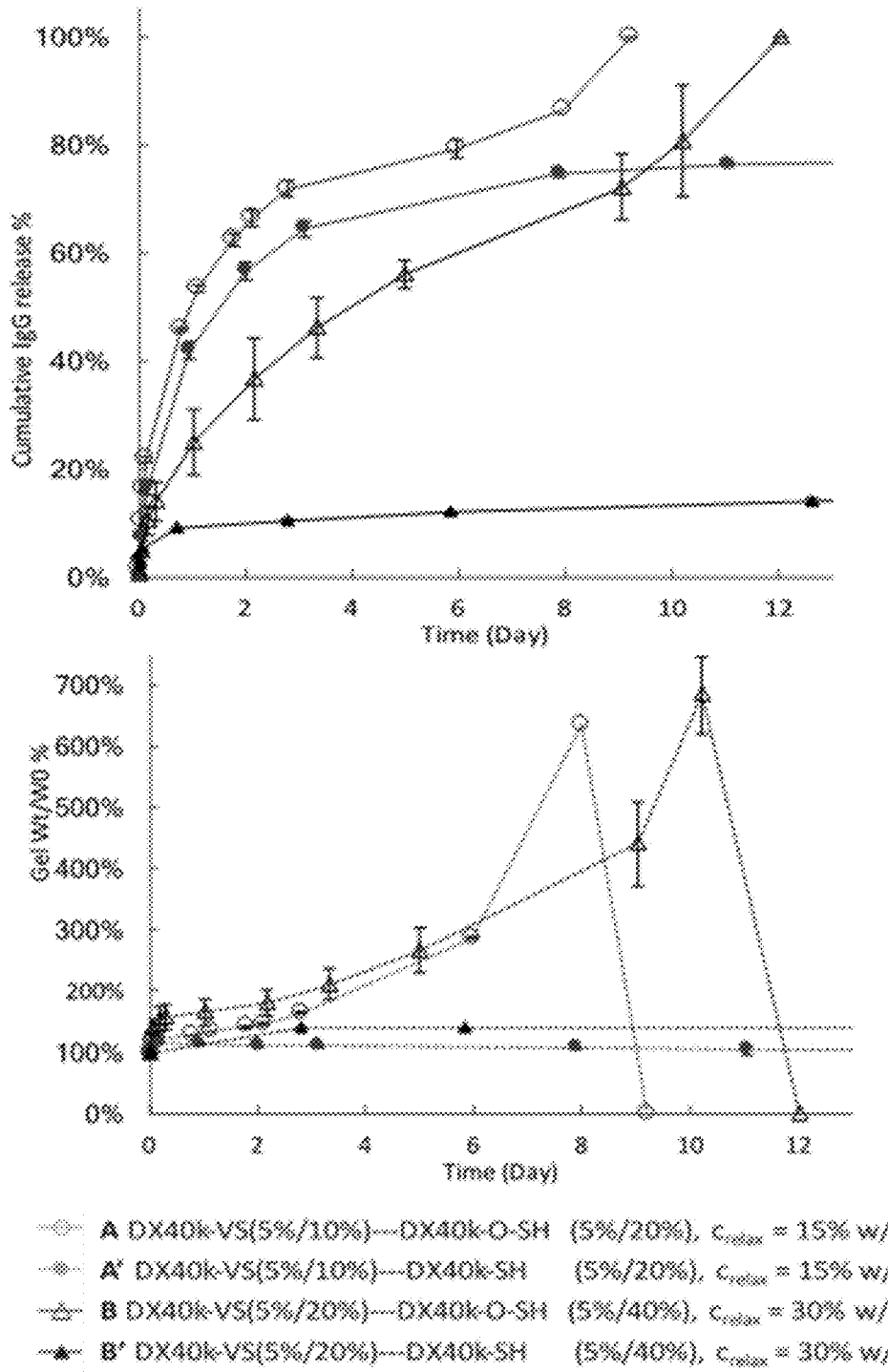
FIG. 11 illustrates the release profile of IgG and swelling profile of junction-lysable and non-degradable formulations.

The IgG release profile of junction-lysable hydrogels were compared with their corresponding non-degradable formulations with same polymer concentration and DM (FIG. 11). The degradable feature added extra complexities to the laden protein release, as the meshwork had become dynamic. The release curve of IgG from 15% w/v junction-lysable and non-degradable hydrogels overlapped well during early to midterm phases. The burst release in the first two days dominated the major release in the early phase. In the later stage of degradation (>300% swelling ratio), the hydrogel meshwork started to lose its integrity and rapidly dumped out all the remaining IgG molecules upon the collapse of hydrogel. If polymer concentration was increased to 30%, the degradable hydrogel gave a different release profile comparing to its non-degradable counterpart. As the meshwork in 30 w/v % hydrogel was empirically dense enough to suppress the burst release, we attributed the continuous release to the meshwork degradation.

FIG. 11 illustrates the release profile of IgG (left, solid lines) and swelling profile (right, dotted lines) of junction-lysable (A&B) and non-degradable (A'&B') formulations in PBS at 37° C. Hydrogel formulations are presented as (DM/polymer concentration). $c_{relax}$ is the polymer concentration in hydrogels at relax state. Error bars represent one SD from the mean.

Figure 14:
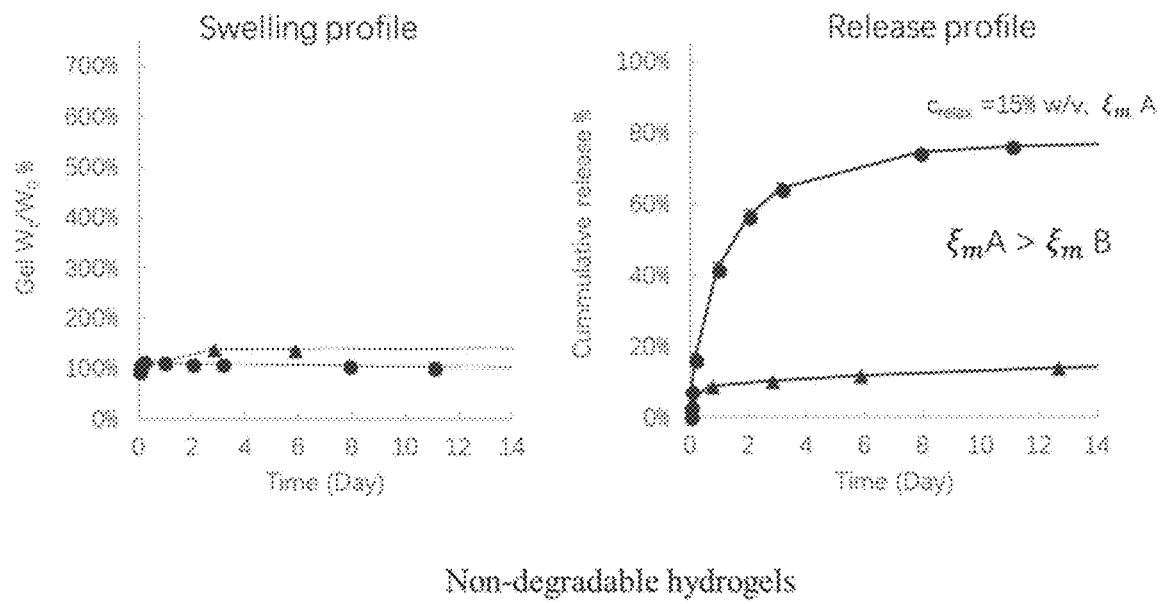
FIG. 14 illustrates the result of the release of IgG from non-degradable and hydrolysable hydrogels.

The result of the release of IgG from non-degradable and hydrolysable hydrogels is also indicated in FIG. 14.

Figure 21:
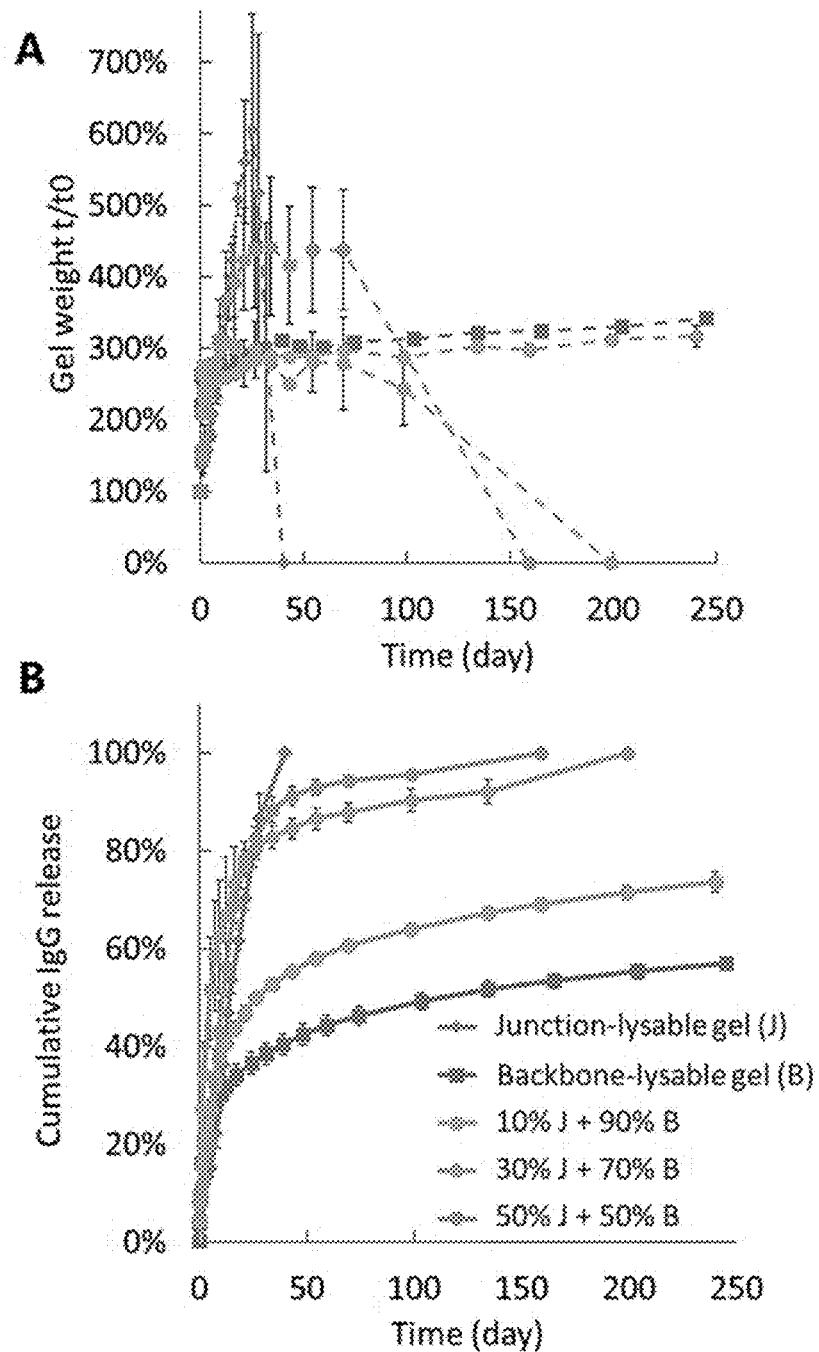

The IgG release profile of hydrolytically degradable hydrogels were compared with their corresponding non-degradable formulations (FIG. 21A-21B). For example, 10% J+90% B represents a mixed hydrogel which the ration of the hydrolysable hydrogels and the non-degradable hydrogels was about 1:9 in mass when mixing.

The result of the release of IgG in FIG. 21A-21B illustrates that the release profile can be manipulated with the ratio of the hydrolysable hydrogels and the non-degradable hydrogels. And the release rate of IgG protein was dominated by bulk degradation rate.

Example 9 IgG Release Effected by Alternative pH Buffers

Figure 12:
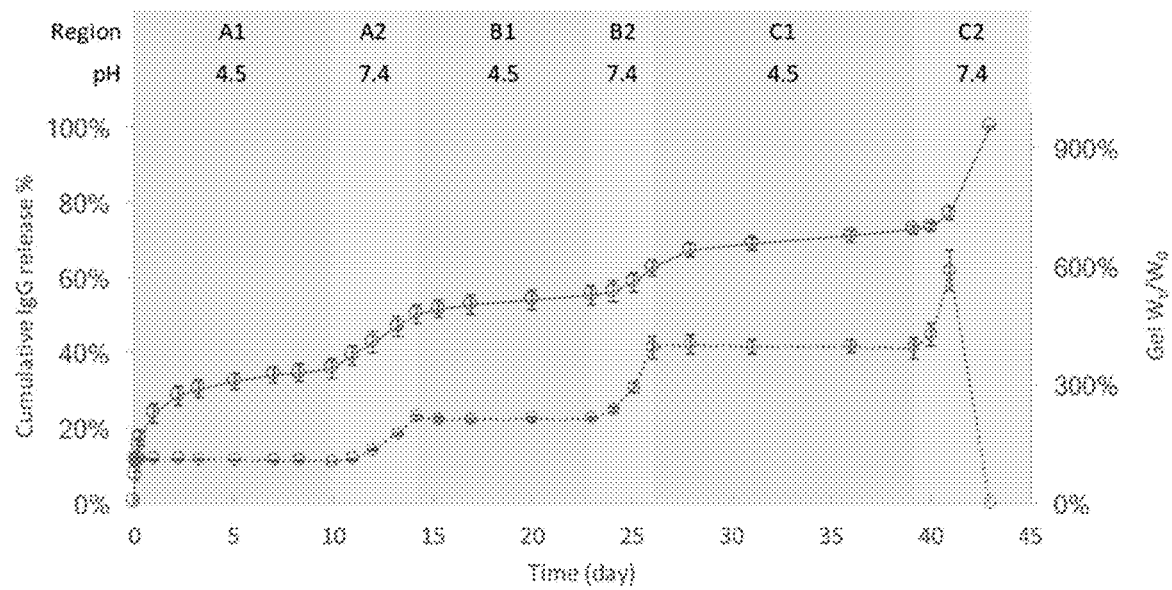
FIG. 12 illustrates swelling profile of junction-lysable hydrogel and the release of IgG in releasing buffer with alternative changed pH.

To further confirm that the IgG release was meshwork degradation dependent, the IgG release was measured from a junction-lysable hydrogel incubated in alternative pH buffers (FIG. 12). The hydrolysis rate constant of the methacrylate derived esters were approximately $8\times10^{-5}$ day$^{-1}$ and $4\times10^{-2}$ day$^{-1}$ at pH 4.5 and 7.4 respectively under 37° C. (refers to W. N. van Dijk-Wolthuis, M. J. van Steenbergen, W. J. Underberg, and W. E. Hennink, "Degradation kinetics of methacrylated dextrans in aqueous solution.," *J. Pharm. Sci.*, vol. 86, no. 4, pp. 413-7, 1997), so that the hydrogel degradation was halted and resumed according to pH change. Therefore, the IgG release profile from steady and degrading hydrogel meshworks were compared directly. Discount the initial burst, the IgG release rate in pH 7.4 regions were significantly faster than in pH 4.5 regions, which agreed with the hypothesis that meshwork degradation dominated the laden IgG release. Another interesting point was that the laden IgG release rate was independent to the mean mesh size. According to above equation 1, mean mesh size would inflate by $Q_r$ ⅓. Therefore, mean mesh size in region C1>B1>A1, but the slopes of release curves were similar. On the contrary, the mesh size in region B1 should be larger than in A1, but the A1 slope was steeper than B1, indicating the rate of mesh opening was the rate limiting step.

FIG. 12 illustrates the swelling profile of junction-lysable hydrogel and the release of IgG in releasing buffer with alternative changed pH. Formulation details: DX40k-VS (5% DM/10% w/v) crosslinked with DX40k-O-SH (8% DM/20% w/v).

Example 10 Measuring Hydrolysis Rate of Esters in Hydrogel by Mass Swelling Test The hydrogel using the polymers prepared in example 1-3 were prepared according to the formulation in Table 2.

TABLE 2

| Group | Formulation | Polymer Concentration w/v % | VS:SH DM ratio |
|---|---|---|---|
| JL-1 | DX40k-VS_ DX40k-O-SH | 15 | 5:8 |
| JL-2 | DX40k-VS_ DX40k-O-SH | 30 | 5:8 |
| JL-3 | DX40k-VS_ DX40k-O-SH | 15 | 10:8 |
| JL-4 | DX40k-VS_ DX40k-O-SH | 15 | 9:8 |
| JL-5 | DX150k-VS_ DX150k-O-SH | 15 | 8:8 |
| JL-6 | DX150k-VS_ DX150k-O-SH | 15 | 15:8 |

Then the hydrogels were incubated pH 7.4 PBS/0.02 w/v % NaN$_3$ at 37° C. Hydrogel wet weight at various time points were measured. The surface liquid on hydrogels was carefully drained dried with tissue paper. The collapsing time was defined as the time when the hydrogel was too weak to handle.

Figure 19:
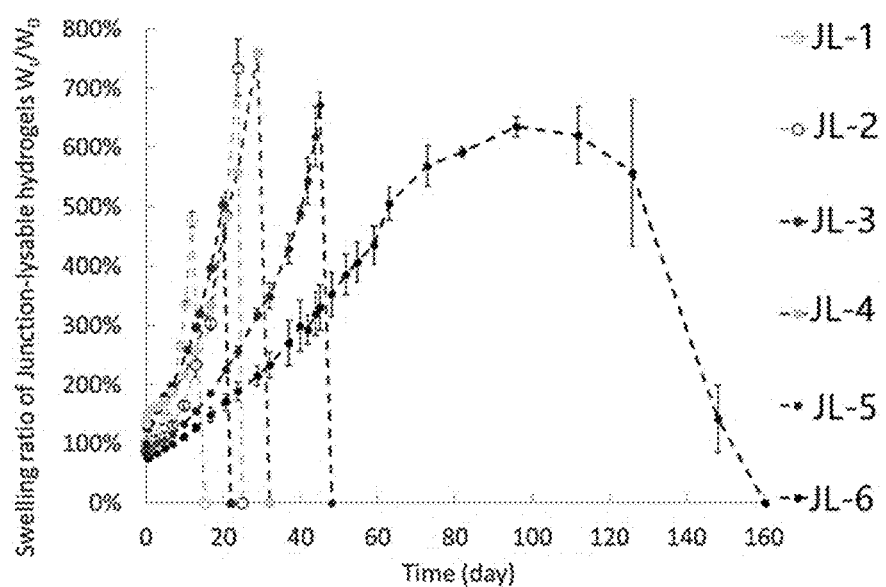
FIG. 19 illustrates hydrogel swelling profile of the junction-lysable hydrogels.

FIG. 19 illustrates hydrogel swelling profile of the junction-lysable hydrogels. Form the result of FIG. 19, it can be indicated that the formulation JL-6 had same chemistry of hydrolysable esters consisting junctions between the polymers.

Hence, the hydrolysis rate of esters in hydrogel can be tuned by manipulating the structural parameters, such as the molecular weight, polymer concentration and degree of modification.

The hydrogel using the polymers prepared in example 1-3 were prepared according to the formulation in Table 3. BL-1~BL-4 were varied in the degradable linker in the degradable backbone.

TABLE 3

| Group | Formulation | linker | Polymer Concentration w/v % | VS:SH DM ratio |
|---|---|---|---|---|
| BL-1 | DX6k-VS_DX40k-O-SH | DTT-VMA-DTT | 20 | 5:4 |
| BL-2 | DX6k-VS_DX40k-O-SH | DTP-VMA-DTP | 25 | 5:4 |
| BL-3 | DX6k-VS_DX40k-O-SH | DTE-VA-DTE | 25 | 5:4 |
| BL-4 | DX6k-VS_DX40k-O-SH | DTE-VMA-DTE | 20 | 4:4 |

Figure 20:
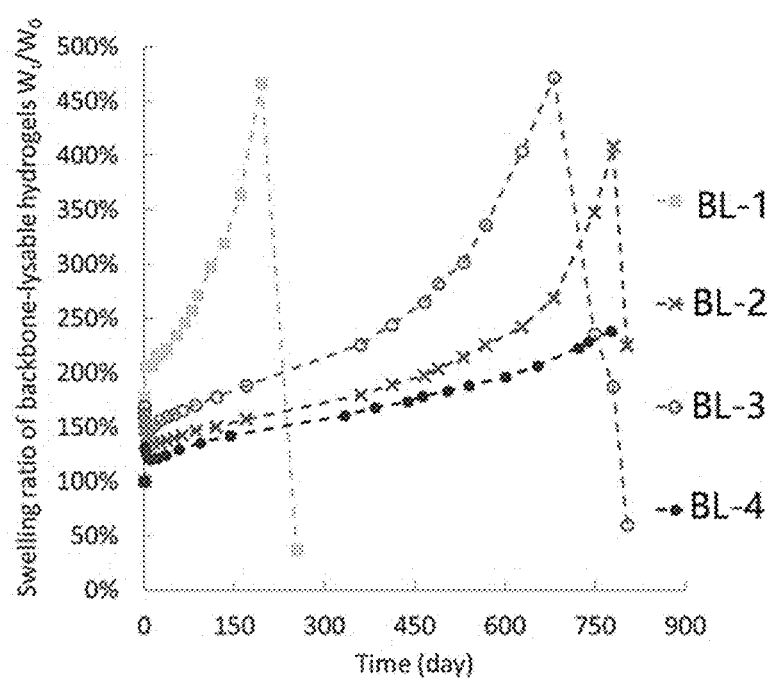
FIG. 20 illustrates hydrogel swelling profile of the backbone-lysable hydrogels.

Then the hydrogels were incubated pH 7.4 PBS/0.02 w/v % NaN$_3$ at 37° C. Hydrogel wet weight at various time points were measured. The surface liquid on hydrogels was carefully drained dried with tissue paper. The collapsing time was defined as the time when the hydrogel was too weak to handle. FIG. 20 illustrates hydrogel swelling profile of the backbone-lysable hydrogels.

The hydrogel using the polymers prepared in example 1-3 were prepared. The hydrogels were varied in the degradable linker in the degradable backbone.

Figure 16:
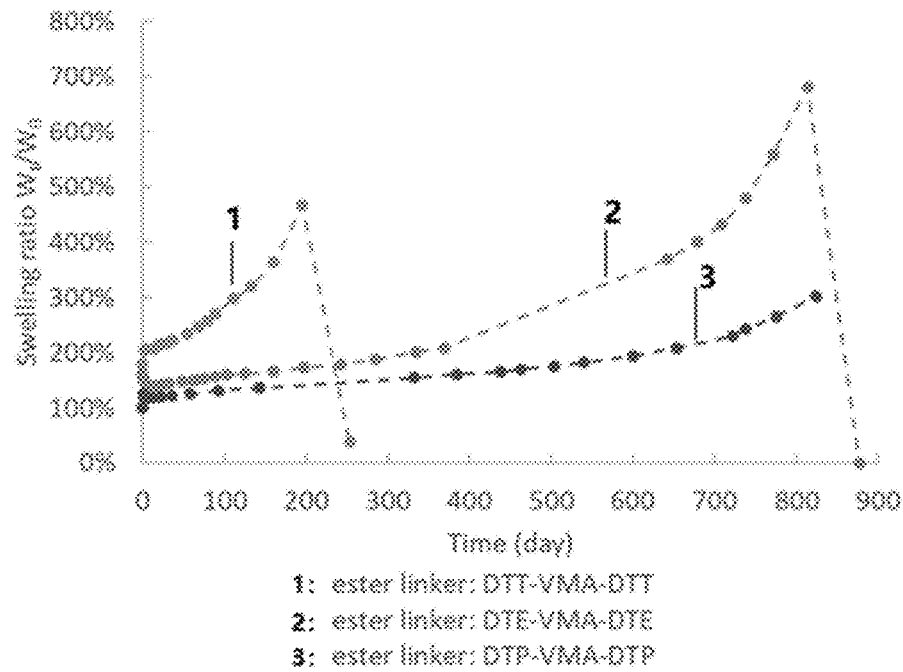
FIG. 16 illustrates hydrogel swelling profile of the backbone-lysable hydrogels.

Then the hydrogels were incubated pH 7.4 PBS/0.02 w/v % NaN$_3$ at 37° C. Hydrogel wet weight at various time points were measured. The surface liquid on hydrogels was carefully drained dried with tissue paper. The collapsing time was defined as the time when the hydrogel was too weak to handle. FIG. 16 illustrates hydrogel swelling profile of the backbone-lysable hydrogels.

Example 11 Measuring Hydrolytic Half-Life

The hydrolytic half-life was measured in 0.2M phosphate buffer (pH 7.4) in D$_2$O at 37° C.

Table 4 illustrates the result of hydrolytic half-life of different degradable linkers:

TABLE 4

| the structure of degradable linkers | hydrolytic half-life |
|---|---|
| Dextran—O—C(=O)—CH(CH$_3$)—CH$_2$—S—CH$_2$CH$_2$—SH | about 14 days |
| Dextran—O—C(=O)—CH(CH$_3$)—CH$_2$—S—CH$_2$CH$_2$CH$_2$—SH | about 16 days |
| Dextran—O—C(=O)—CH(CH$_3$)—CH$_2$—S—CH$_2$—CH(OH)—SH | about 11 days |
| Dextran—O—C(=O)—CH(CH$_3$)—CH$_2$—S—CH$_2$—CH(OH)—CH(OH)—CH$_2$—SH | about 10 days |
| Dextran—O—CH$_2$CH$_2$—SO$_2$—CH$_2$CH$_2$—S—CH$_2$CH$_2$—S—CH$_2$—CH(CH$_3$)—C(=O)—O—CH=CH$_2$ | about 6 days |
| Dextran—O—CH$_2$CH$_2$—SO$_2$—CH$_2$CH$_2$—S—CH$_2$CH$_2$CH$_2$—S—CH$_2$—CH(CH$_3$)—C(=O)—O—CH=CH$_2$ | about 6 days |
| Dextran—O—CH$_2$CH$_2$—SO$_2$—CH$_2$CH$_2$—S—CH$_2$—CH(OH)—CH(OH)—CH$_2$—S—CH$_2$—CH(CH$_3$)—C(=O)—O—CH=CH$_2$ | about 5 days |
| Dextran—O—CH$_2$CH$_2$—SO$_2$—CH$_2$CH$_2$—S—CH$_2$CH$_2$—S—CH$_2$—CH(CH$_3$)—C(=O)—O—CH$_2$CH$_2$—S—CH$_2$CH$_2$—SH | low solubility in aqueous buffers |

TABLE 4-continued

| the structure of degradable linkers | hydrolytic half-life |
|---|---|
| 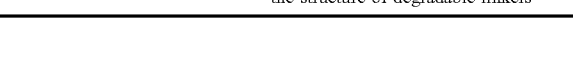 | about 190 days |
| 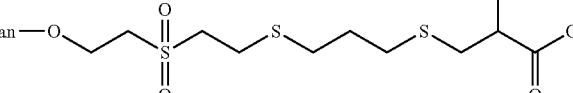 | about 60 days |

From the result of table 4, it is indicated that the modulator modified only on one side of the ester has little effect on ester hydrolysis rate of the degradable linker, while the modulator modified on both sides of the ester facilitate the stabilization of the degradable linker significantly. And it is indicated that the hydrophobic modulator is more helpful to stabilize the degradable linker than the hydrophilic modulator. However, the hydrophobic modulator may reduce the solubility of the degradable linker in aqueous buffers.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A composition comprising one or more hydrogel forming polymers, said hydrogel enables sustained release of a target agent, at least one of said one or more hydrogel forming polymers comprises a degradable backbone, and wherein said degradable backbone comprises precursor polymers linked by a degradable linker,
    wherein said hydrogel forming polymer is selected from the group consisting of a polysaccharide, a polyethylene glycol, a derivative thereof, and any combinations thereof;
    comprising at least a first hydrogel forming polymer derivative and a second hydrogel forming polymer derivative, wherein said first hydrogel forming polymer derivative comprises a first modification and said second hydrogel forming polymer derivative comprises a second modification, said first modification is different from said second modification, and said first polymer derivative is capable of reacting with said second polymer derivative to form said hydrogel;
    wherein a mass ratio between said first hydrogel forming polymer derivative and said second hydrogel forming polymer derivative in said composition is from about 3:1 to about 1:3; or
    wherein a molar ratio between said first hydrogel forming polymer derivative and said second hydrogel forming polymer derivative in said composition is from about 10:1 to about 1:10; or
    wherein a volume ratio between said first hydrogel forming polymer derivative and said second hydrogel forming polymer derivative in said composition is from about 3:1 to about 1:3; or
    wherein said first hydrogel forming polymer derivative has a first DM, said second hydrogel forming polymer derivative has a second DM, and a ratio between said first DM and said second DM is from about 3:1 to about 1:3.

2. The composition according to claim 1,
    wherein said hydrogel forming polymer comprising the degradable backbone is formed by cross linking said precursor polymers with said degradable linker, wherein said degradable linker enables formation of degradable linkage between said precursor polymers and
    wherein said degradable linker comprises two or more modifications, and a degree of modification of said degradable linker is less than about 30%; wherein said modification of said degradable linker is selected from the group consisting of an acrylate, a methacrylate, a maleimide, a vinylsulfone, a thiol, an amine, and any combinations thereof.

3. The composition according to claim 1, wherein said degradable linker is selected from the following groups:

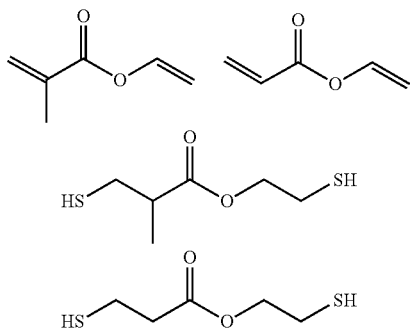

-continued

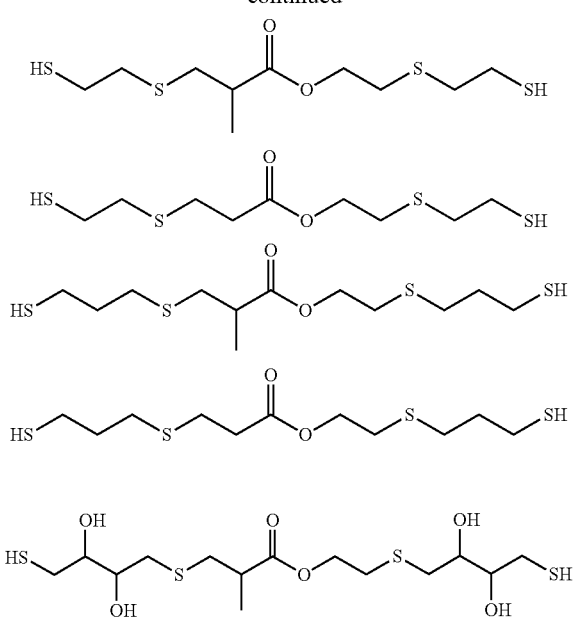

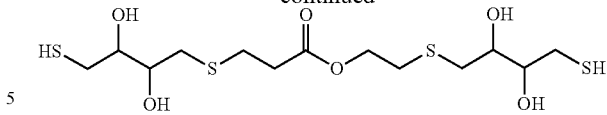

4. A hydrogel for sustained release of a target agent, wherein said hydrogel is formed with the composition according to claim 1.

5. The hydrogel according to claim 4, wherein about less than 30% of said target agent is cumulatively released within an initial 24 hours from said hydrogel, and the remaining portion of said target agent is cumulatively released from said hydrogel in about 3 to about 36 months.

6. A method for producing a composition according to claim 1, comprising:
   a) crosslinking the precursor polymer with the degradable linker to obtain the hydrogel forming polymer comprising the degradable backbone; and
   b) mixing said hydrogel forming polymer comprising the degradable backbone with an additional polymer, wherein said additional polymer is capable of reacting with said hydrogel forming polymer comprising the degradable backbone under a condition enabling formation of the hydrogel.

* * * * *